US012655154B2

(12) United States Patent
Jagusch et al.

(10) Patent No.: US 12,655,154 B2
(45) Date of Patent: Jun. 16, 2026

(54) CRYSTALLINE SOLVATED FORMS OF N-(4-(1-(2,6-DIFLUOROBENZYL)-5-((DIMETHYLAMINO)METHYL)-3-(6-METHOXY-3-PYRIDAZINYL)-2,4-DIOXO-1,2,3,4-TETRAHYDROTHIENO[2,3-D]PYRIMIDIN-6-YL)PHENYL)-N'-METHOXYUREA

(71) Applicant: Sumitomo Pharma Co., Ltd., Osaka (JP)

(72) Inventors: Carsten Jagusch, Schwabach (DE); Christian Klaus Herz, Neuendettelsau (DE); Andreas Schrodt, Burgthann (DE); Petinka I. Vlahova, West Lafayette, IN (US); Sven Stirnweiss, Fürth (DE)

(73) Assignee: Sumitomo Pharma Co., Ltd., Osaka (JP)

( * ) Notice: Subject to any disclaimer, the term of this patent is extended or adjusted under 35 U.S.C. 154(b) by 1105 days.

(21) Appl. No.: 17/716,965

(22) Filed: Apr. 8, 2022

(65) Prior Publication Data

US 2022/0372044 A1 Nov. 24, 2022

Related U.S. Application Data

(63) Continuation of application No. PCT/EP2020/078475, filed on Oct. 9, 2020.

(60) Provisional application No. 62/913,606, filed on Oct. 10, 2019.

(51) Int. Cl.
*C07D 495/04* (2006.01)

(52) U.S. Cl.
CPC ........ *C07D 495/04* (2013.01); *C07B 2200/13* (2013.01)

(58) Field of Classification Search
CPC .......................... C07D 495/04; C07B 2200/13
See application file for complete search history.

(56) References Cited

U.S. PATENT DOCUMENTS 3,872,115 A 3/1975 Sugimoto et al.
5,312,958 A 5/1994 Suenaga et al.
6,297,379 B1 10/2001 Furuya et al.
6,340,686 B1 1/2002 Furuya et al.
7,300,935 B2 11/2007 Cho et al.
7,569,570 B2 8/2009 Furuya et al.
8,058,280 B2 11/2011 Cho et al.
8,735,401 B2 5/2014 Cho et al.
9,346,822 B2 5/2016 Cho et al.
9,758,528 B2 * 9/2017 Fukuoka .............. C07D 333/38
10,150,778 B2 12/2018 Miwa
10,160,765 B2 12/2018 Enlow et al.
10,350,170 B2 7/2019 Yamane et al.
10,449,191 B2 10/2019 Rajasekhar et al.
10,464,945 B2 11/2019 Miwa
10,544,160 B2 1/2020 Miwa
10,689,359 B2 6/2020 Shu et al.
10,786,501 B2 9/2020 Rajasekhar et al.
11,033,551 B2 6/2021 Johnson et al.
11,053,257 B2 7/2021 Miwa
11,583,526 B2 2/2023 Rajasekhar et al.
11,655,256 B1 5/2023 Paschalides
11,731,983 B2 8/2023 Miwa
11,793,812 B2 10/2023 Johnson et al.
11,795,178 B2 10/2023 Fukuoka et al.
11,957,684 B2 4/2024 Johnson et al.
12,097,198 B2 9/2024 Rajasekhar et al.
12,144,809 B1 11/2024 Rajasekhar et al.
12,180,224 B2 12/2024 Fukuoka et al.
12,325,714 B2 6/2025 Miwa
12,336,990 B2 6/2025 Rajasekhar et al.
12,338,249 B2 6/2025 Brandl et al.
2003/0055269 A1 3/2003 Fukuoka et al.
2004/0014634 A1 1/2004 Bantick et al.
2006/0160829 A1 7/2006 Cho et al.
2008/0287465 A1 11/2008 Tumey et al.
2009/0048273 A1 2/2009 Furuya et al.
2011/0172249 A1 7/2011 Kamikawa et al.
2015/0266891 A1 9/2015 Fukuoka et al.
2017/0210753 A1 7/2017 Fukuoka et al.
2019/0224196 A1 7/2019 Rajasekhar et al.
2019/0262346 A1 8/2019 Johnson et al.
2020/0000730 A1 1/2020 Yamane et al.
2021/0205303 A1 7/2021 Rajasekhar et al.
2021/0401841 A1 12/2021 Johnson et al.
2022/0135585 A1 5/2022 Miwa
2022/0204525 A1 6/2022 Fukuoka et al.
2022/0227784 A1 7/2022 Kantor et al.
2022/0396582 A1 12/2022 Brandl et al.
(Continued)

FOREIGN PATENT DOCUMENTS

CA 3010509 A1 7/2017
CN 87101864 A 11/1987
(Continued)

OTHER PUBLICATIONS

Byrn, S. et al. (1995). "Pharmaceutical solids: A Strategic Approach to Regulatory Considerations," Pharma. Res. 12:945-954.
(Continued)

*Primary Examiner* — Sarah Pihonak
*Assistant Examiner* — Mikhail O'Donnel Robinson
(74) *Attorney, Agent, or Firm* — Cooley LLP

(57) ABSTRACT

This disclosure relates to crystalline solvated forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea. It also relates to methods of making the disclosed crystalline forms, pharmaceutical compositions and kits comprising the forms, and methods of treatment and uses comprising their administration.

19 Claims, 7 Drawing Sheets

(56) References Cited

U.S. PATENT DOCUMENTS

| | | | |
|---|---|---|---|
| 2023/0165800 | A1 | 6/2023 | Alonzo et al. |
| 2023/0212184 | A1 | 7/2023 | Fukuoka et al. |
| 2024/0165118 | A1 | 5/2024 | Johnson et al. |
| 2025/0051353 | A1 | 2/2025 | Miwa |
| 2025/0057839 | A1 | 2/2025 | Rajasekhar et al. |
| 2025/0066382 | A1 | 2/2025 | Vlahova et al. |
| 2025/0082632 | A1 | 3/2025 | Rajasekhar et al. |
| 2025/0332166 | A1 | 10/2025 | Rajasekhar et al. |
| 2025/0368660 | A1 | 12/2025 | Miwa |

FOREIGN PATENT DOCUMENTS

| | | | | |
|---|---|---|---|---|
| CN | 1349536 A | 5/2002 | | |
| CN | 1406239 A | 3/2003 | | |
| CN | 1551883 A | 12/2004 | | |
| CN | 1761671 A | 4/2006 | | |
| CN | 1768065 A | 5/2006 | | |
| CN | 101048065 A | 10/2007 | | |
| CN | 110248661 A | 9/2019 | | |
| CN | 111333633 A | 6/2020 | | |
| CN | 111423452 A | 7/2020 | | |
| CN | 112552312 A | 3/2021 | | |
| CN | 115417883 A | 12/2022 | | |
| CN | 115947734 A | 4/2023 | | |
| EP | 1 266 898 A1 | 12/2002 | | |
| EP | 1 591 446 A1 | 11/2005 | | |
| EP | 3 666 776 A1 | 6/2020 | | |
| IN | 31/2023 | 8/2023 | | |
| JP | H-06-192170 A | 7/1994 | | |
| JP | H-10-298156 A | 11/1998 | | |
| JP | 2001-278884 A | 10/2001 | | |
| JP | 2001-316391 A | 11/2001 | | |
| JP | 2002-088044 A | 3/2002 | | |
| JP | 2010-229098 A | 10/2010 | | |
| JP | 2015-532262 A | 11/2015 | | |
| JP | 2016-041720 A | 3/2016 | | |
| JP | 2017-088564 A | 5/2017 | | |
| JP | 2018-538348 A | 12/2018 | | |
| JP | 2019-038825 A | 3/2019 | | |
| JP | 2019-511510 A | 4/2019 | | |
| WO | WO-00/56739 A1 | 9/2000 | | |
| WO | WO-2004/067535 A1 | 8/2004 | | |
| WO | WO-2007/011072 A1 | 1/2007 | | |
| WO | WO-2010/026993 A1 | 3/2010 | | |
| WO | WO-2014/051164 A2 | 4/2014 | | |
| WO | WO-2014/051164 A3 | 4/2014 | | |
| WO | WO-2016/136849 A1 | 9/2016 | | |
| WO | WO-2017/172615 A1 | 10/2017 | | |
| WO | WO-2018/060463 A2 | 4/2018 | | |
| WO | WO-2018/060463 A3 | 4/2018 | | |
| WO | WO-2018/060501 A2 | 4/2018 | | |
| WO | WO-2018/060501 A3 | 4/2018 | | |
| WO | WO-2019178304 A1 * | 9/2019 | ........... | C07D 495/04 |
| WO | WO-2020/0230094 A1 | 11/2020 | | |
| WO | WO-2021/026011 A1 | 2/2021 | | |
| WO | WO-2021/027937 A1 | 2/2021 | | |
| WO | WO-2021/031148 A1 | 2/2021 | | |
| WO | WO-2021/069700 A1 | 4/2021 | | |
| WO | WO-2021/069711 A1 | 4/2021 | | |
| WO | WO-2021/239917 A1 | 12/2021 | | |
| WO | WO-2022/101303 A1 | 5/2022 | | |
| WO | WO-2022/166121 A1 | 11/2022 | | |
| WO | WO-2023/042214 A1 | 3/2023 | | |
| WO | WO-2023/066941 A1 | 4/2023 | | |
| WO | WO-2023/119333 A1 | 6/2023 | | |
| WO | WO-2023/194924 A1 | 10/2023 | | |

OTHER PUBLICATIONS

Caira, M.R. (1998). "Crystalline polymorphism of organic compounds," Topics in Curr. Chem. 198:163-208.

Chinese Office Action mailed on Nov. 17, 2016, for Chinese patent application No. 201380051107.2, filed on Sep. 27, 2013, 14 pages (with English translation).

Ex Parte Quayle Action mailed on Jun. 5, 2018, for U.S. Appl. No. 15/481,505, filed Apr. 7, 2017, 4 pages.

Extended European Search Report mailed on Nov. 9, 2018, for EP Application No. 18 185 835.8, filed on Sep. 27, 2013, 5 pages.

Holzer, G. et al. (1997). "$K\alpha_{1,2}$ and $K\beta_{1,3}$ X-ray emission lines of the 3d transition metals," Phys. Rev. A56(6):4554-4568.

International Search Report mailed on Mar. 24, 2014, for PCT Application No. PCT/JP2013/077013, filed on Sep. 27, 2013, 7 pages.

International Search Report mailed on Jan. 25, 2021, for PCT Application No. PCT/EP2020/078493, filed on Oct. 9, 2020, 6 pages.

International Search Report mailed on Jan. 25, 2021, for PCT Application No. PCT/EP2020/078475, filed on Oct. 9, 2020, 6 pages.

Liu Xin-yong et al. (2011). Laboratory Preparation, Separation and Purification Technology of Organic Compounds, People's Medical Publishing House, pp. 103-106 (with English translation).

Miwa, K. et al. (2011). "Discovery of 1-{4-[1-(2,6-Difluorobenzyl)-5-[(dimethylamino)methyl]-3-(6-methoxypyridazin-3-yl)-2,4-dioxo-1,2,3,4-tetrahydrothieno[2,3-d ]pyrimidin-6-yl]phenyl}-3-methoxyurea (TAK-385) as a Potent, Orally Active, Non-Peptide Antagonist of the Human Gonadotropin-Releasing Hormone Receptor," J. Med. Chem. 54:4998-5012.

Non-Final Office Action mailed on May 12, 2016, for U.S. Appl. No. 14/432,188, filed Mar. 27, 2015, 4 pages.

Non-Final Office Action mailed on Nov. 21, 2017, for U.S. Appl. No. 15/481,505, filed Apr. 7, 2017, 7 pages.

Non-Final Office Action mailed on Mar. 22, 2019, for U.S. Appl. No. 16/034,002, filed Jul. 12, 2018, 4 pages.

Non-Final Office Action mailed on Jun. 6, 2019, for U.S. Appl. No. 16/116,804, filed Aug. 29, 2018, 6 pages.

Non-Final Office Action mailed on Aug. 24, 2020, for U.S. Appl. No. 16/710,390, filed Dec. 11, 2019, 4 pages.

Notice of Allowance mailed on May 17, 2017, for U.S. Appl. No. 14/432,188, filed Mar. 27, 2015, 5 pages.

Notice of Allowance mailed on Sep. 17, 2018, for U.S. Appl. No. 15/481,505, filed Apr. 7, 2017, 5 pages.

Notice of Allowance mailed on Jul. 3, 2019, for U.S. Appl. No. 16/034,002, filed Jul. 12, 2018, 5 pages.

Notice of Allowance mailed on Sep. 12, 2019, for U.S. Appl. No. 16/116,804, filed Aug. 29, 2018, 6 pages.

Notice of Allowance mailed on Nov. 26, 2019, for U.S. Appl. No. 16/116,804, filed Aug. 29, 2018, 2 pages.

Notice of Allowance mailed on Mar. 10, 2021, for U.S. Appl. No. 16/710,390, filed Dec. 11, 2019, 6 pages.

Written Opinion of the International Searching Authority mailed on Mar. 24, 2014, for PCT Application No. PCT/JP2013/077013, filed on Sep. 27, 2013, 10 pages.

Written Opinion of the International Searching Authority mailed on Jan. 25, 2021, for PCT Application No. PCT/EP2020/078493, filed on Oct. 9, 2020, 10 pages.

Written Opinion of the International Searching Authority mailed on Jan. 25, 2021, for PCT Application No. PCT/EP2020/078475, filed on Oct. 9, 2020, 11 pages.

Yang, Lv et al. (2009). Polymorphic Drugs, People's Medical Publishing House, pp. 24-25 (with English translation).

U.S. Appl. No. 17/349,584, filed Jun. 16, 2021, by Fukuoka et al.

U.S. Appl. No. 17/716,963, filed Apr. 8, 2022, by Brandl et al.

Corrected Notice of Allowability mailed on Jul. 12, 2023, for U.S. Appl. No. 17/349,584, filed Jun. 16, 2021, 2 pages.

Corrected Notice of Allowability mailed on Sep. 1, 2023, for U.S. Appl. No. 17/694,635, filed Mar. 14, 2022, 2 pages.

Ding, Z. et al. (Oct. 22, 2018). "Crystalline forms," Chinese Pharmaceutical Journal, pp. 85 (with English Translation).

Extended European Search Report mailed on Nov. 25, 2022, for EP Application No. 22 168 256.0, filed on Sep. 27, 2013, 8 pages.

Guo, Z. et al. (2003). "Synthesis and structure-activity relationships of Thieno[2,3-d]pyrimidine-2,4-dione derivatives as potent GnRH receptor antagonists," Bioorganic & Medicinal Chemistry Letters 13:3617-3622.

Hirayama, N. (2008). Organic Compound Crystal Production Handbook, 32 pages (English Summary Provided).

(56) References Cited

OTHER PUBLICATIONS

Huang Li et al. (Nov. 18, 2018). "Progress in the study of new drug therapies for endometriosis," The Journal of Practical Medicine, vol. 34, No. 21, pp. 164-167 (with English Abstract Provided).
International Search Report mailed on Jan. 26, 2023, for PCT Application No. PCT/EP2022/078989, filed on Oct. 18, 2022, 4 pages.
Kumar, J.S et al. (2001). "Simple and chemoselective reduction of aromatic nitro compounds to aromatic amines: Reduction with hydriodic acid revisited," Tetrahedron Letter 42:5601-5603.
Non-Final Office Action mailed on Apr. 10, 2023, for U.S. Appl. No. 17/349,584, filed Jun. 16, 2021, 7 pages.
Non-Final Office Action mailed on Jul. 18, 2024, for U.S. Appl. No. 18/121,886, filed Mar. 15, 2023, 6 pages.
Notice of Allowance mailed on May 10, 2023, for U.S. Appl. No. 17/349,584, filed Jun. 16, 2021, 5 pages.
Notice of Allowance mailed on Aug. 17, 2023, for U.S. Appl. No. 17/694,635, filed Mar. 14, 2022, 6 pages.
Notice of Allowance mailed on Aug. 21, 2024, for U.S. Appl. No. 18/121,886, filed Mar. 15, 2023, 5 pages.
Sasaki, S. et al. (2002). "Discovery of a thieno[2,3-d]pyrimidine-2,4-dione bearing a p-methoxyureidophenyl moiety at the 6-position: a highly potent and orally bioavailable non-peptide antagonist for the human luteinizing hormone-releasing hormone receptor ,"J. Med. Chem. 46:113-124.
Serizawa, K. (2002). Optimization of salt and crystal forms and crystallization techniques, Pharm. Tech. Japan, vol. 18, No. 10, pp. 81-96 (with English Abstract Provided).
Written Opinion of the International Searching Authority mailed on Jan. 26, 2023, for PCT Application No. PCT/EP2022/078989, filed on Oct. 18, 2022, 8 pages.
Zhang Hongli et al. (Dec. 31, 2016). "Microstructure and performance in the desolvation process of HNS/dioxane solvate by In-situ XRD method," Chinese Journal of Energetic Materials, vol. 24, No. 4, pp. 363-367 (with English Abstract Provided).
U.S. Appl. No. 18/195,654, filed May 10, 2023, by Migoya et al.
U.S. Appl. No. 18/392,110, filed Dec. 21, 2023, by Migoya et al.
U.S. Appl. No. 18/427,033, filed Jan. 30, 2024, by Johnson et al.
U.S. Appl. No. 18/636,642, filed Apr. 16, 2024, by Vlahova et al.
U.S. Appl. No. 18/758,904, filed Jun. 28, 2024, by Rajasekhar et al.
U.S. Appl. No. 18/792,752, filed Aug. 2, 2024, by Rajasekhar et al.
U.S. Appl. No. 18/797,045, filed Aug. 7, 2024, by Migoya et al.
U.S. Appl. No. 18/926,157, filed Oct. 24, 2024, by Johnson et al.
U.S. Appl. No. 18/927,346, filed Oct. 25, 2024, by Miwa.
Non-Final Office Action mailed on Feb. 11, 2025, for U.S. Appl. No. 18/927,346, filed Oct. 25, 2024, 6 pages.
Notice of Allowance mailed on Feb. 20, 2025, for U.S. Appl. No. 17/716,963, filed Apr. 8, 2022, 9 pages.
U.S. Appl. No. 19/086,039, filed Mar. 20, 2025, by Migoya et al.
Corrected Notice of Allowability mailed on Apr. 16, 2025, for U.S. Appl. No. 17/716,963, filed Apr. 8, 2022, 6 pages.
U.S. Appl. No. 19/201,728, filed May 7, 2025, by Fukuoka et al.
U.S. Appl. No. 19/212,513, filed May 19, 2025, by Brandl et al.
U.S. Appl. No. 19/228,661, filed Jun. 4, 2025, by Johnson et al.
U.S. Appl. No. 19/399,254, filed Nov. 24, 2025; Inventor Migoya, Elizabeth M. et al.
U.S. Appl. No. 19/449,231, filed Jan. 14, 2026; Inventor Alonzo, David E. et al.

* cited by examiner

CRYSTALLINE SOLVATED FORMS OF N-(4-(1-(2,6-DIFLUOROBENZYL)-5-((DIMETHYLAMINO)METHYL)-3-(6-METHOXY-3-PYRIDAZINYL)-2,4-DIOXO-1,2,3,4-TETRAHYDROTHIENO[2,3-D]PYRIMIDIN-6-YL)PHENYL)-N'-METHOXYUREA

CROSS-REFERENCE TO RELATED APPLICATIONS

This application is a continuation of PCT Patent Application Serial No. PCT/EP2020/078475, filed on Oct. 9, 2020, which claims the benefit of U.S. Provisional Application Ser. No. 62/913,606, filed on Oct. 10, 2019, the entire disclosure of each of which is incorporated herein by reference in its entirety.

This disclosure relates to crystalline solvated forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, also referred to herein as Compound 1. It also relates to methods of making the disclosed crystalline forms, pharmaceutical compositions and kits comprising the forms, and methods of treatment and uses comprising their administration.

BACKGROUND

Compound 1, N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, is a gonadotropin-releasing hormone (GnRH) antagonist being developed as a new pharmaceutical agent useful for treating various conditions including heavy menstrual bleeding and other symptoms associated with uterine fibroids, pain and other symptoms associated with endometriosis, and prostate cancer. Compound 1 may also useful to treat other diseases or disorders. See, e.g., U.S. Pat. Nos. 7,300,935, 8,058,280, 8,735,401, 9,346,822, WO2018060501, and WO2018060463.

Compound 1 and methods of preparing Compound 1 are described in U.S. Pat. Nos. 7,300,935, 8,058,280, 8,735,401, 9,346,822, and 9,758,528.

U.S. Pat. No. 9,758,528, which is herein incorporated by reference in its entirety, describes methods for producing Compound 1 and certain synthetic intermediates, as well as two crystalline forms of Compound 1: a crystal of a tetrahydrofuran (THF) solvate of Compound 1 and a crystal of an anhydrous form of Compound 1 (referred to herein as Form I of Compound 1). For reference, as detailed in U.S. Pat. No. 9,758,528, Form I of Compound 1 may be characterized by an XRPD pattern having peaks at approximately 7.4°, 8.9°, 9.9°, 12.1°, 16.6°, 17.3°, 22.2°, 22.8°, and 27.4° 2θ.

Form I of Compound 1 may also be characterized by the XRPD pattern depicted in FIG. 4 of the present application. Form I of Compound 1 begins to melt at about 189° C. and begins to degrade at about 197° C. Form I of Compound 1 shows an exothermic peak at about 237° C. by DSC with degradation at about 245° C. by TG. FIGS. 5 and 6 show the thermogravimetry (TG) and differential scanning calorimetry (DSC) thermograms, respectively, of Form I of Compound 1.

SUMMARY

An aspect of the disclosure relates to a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XIII of Compound 1. In some embodiments, Form XIII of Compound 1 is characterized by an X-ray power diffraction pattern comprising at least three peaks selected from the group consisting of 5.6°, 5.9°, 9.1°, 11.4° and 14.1° 2θ±0.2° 2θ. In some embodiments, Form XIII of Compound 1 is characterized by an X-ray power diffraction pattern comprising at least five peaks selected from the group consisting of 5.6°, 5.9°, 9.1°, 11.4°, 14.1°, 18.0°, 19.1°, and 21.5° 2θ±0.2° 2θ. In some embodiments, Form XIII of Compound 1 is characterized by an X-ray power diffraction pattern comprising peaks at 5.6°, 5.9°, 9.1°, 11.4° and 14.1° 2θ±0.2° 2θ. In certain such embodiments, the X-ray power diffraction pattern comprises one or more peaks selected from the group consisting of 18.0°, 19.1°, and 21.5°±0.2° 2θ. In some embodiments, Form XIII of Compound 1 is by an XRPD pattern substantially the same as the pattern shown in FIG. 1.

In some embodiments, Form XIII of Compound 1 is characterized by a thermogravimetric thermogram indicating continuous weight loss of about 8.6% between about 32° C. and about 120° C. In some embodiments, Form XIII of Compound 1 is characterized by a TG thermogram substantially the same as the pattern shown in FIG. 2.

In some embodiments, Form XIII of Compound 1 is characterized by an onset of melting between about 99° C. and about 101° C. In some embodiments, Form XIII of Compound 1 is characterized by an onset of melting at about 100° C. In some embodiments, Form XIII of Compound 1 is characterized by a differential scanning calorimetry (DSC) thermogram comprising an endothermic peak between about 105° C. and about 107° C. In some embodiments, Form XIII of Compound 1 is characterized by a DSC thermogram comprising an endothermic peak at about 106° C. In some embodiments, Form XIII of Compound 1 is characterized by a DSC thermogram substantially the same as the pattern shown in FIG. 3.

In some embodiments, Form XIII of Compound 1 is characterized by having at least two of the following:

a) an XRPD pattern comprising at least three peaks selected from the group consisting of 5.6°, 5.9°, 9.1°, 11.4° and 14.1° 2θ±0.2°2θ;

b) an onset of melting at about 100° C. as measured by DSC; and c) an endothermic peak at about 106° C. as measured by DSC.

An aspect of the disclosure relates to a pharmaceutical composition comprising a crystalline form of the disclosure and a pharmaceutically acceptable carrier.

Another aspect of the disclosure relates to a method for preparing Form XIII of Compound 1, said method comprising:

a) suspending a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in DMSO at room temperature;

b) isolating a white suspension resulting from step a); and c) isolating precipitated solids from the white suspension to afford Form XIII of Compound 1.

Another aspect of the disclosure relates to a method for preparing Form XIII of Compound 1, said method comprising:

a) suspending a crystalline form of N-(4-(1-(2,6-difluorobenzyl)-5-((dimethylamino)methyl)-3-(6-methoxy- 3-pyridazinyl)-2,4-dioxo-1,2,3,4-tetrahydrothieno[2,3-d]pyrimidin-6-yl)phenyl)-N'-methoxyurea characterized as Form I of Compound 1 in DMSO at room temperature;

b) isolating a white suspension resulting from step a);

c) subjecting the white suspension to a series of temperature cycles from about 15° C. to about 30° C. to about 15° C., about 10° C. to about 30° C. to about 10° C., and about 5° C. to about 35° C. to about 5° C.; and d) isolating precipitated solids from the white suspension to afford Form XIII of Compound 1.

In some embodiments, there are six temperature cycles from about 15° C. to about 30° C. to about 15° C. In some embodiments, there are six temperature cycles from about 10° C. to about 30° C. to about 10° C. In some embodiments, there are eight temperature cycles from about 5° C. to about 35° C. to about 5° C.

DETAILED DESCRIPTION

Figure 1:
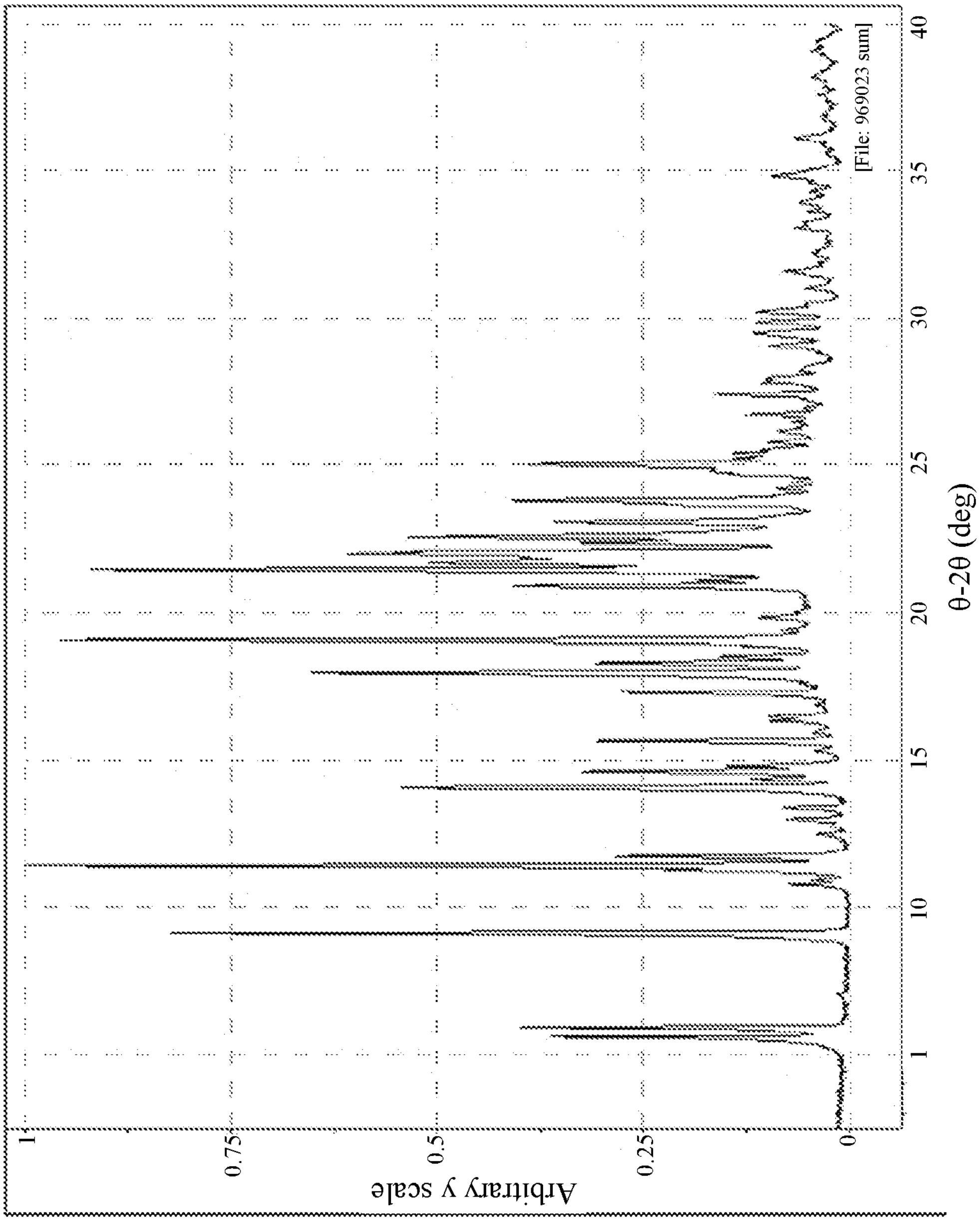
FIG. 1 depicts a powder X-ray diffraction pattern of Form XIII of Compound 1.

Described herein are crystalline solvate forms of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea (Compound 1), methods of making said forms, pharmaceutical compositions and kits comprising said forms, and methods of treatment and uses comprising their administration. The chemical structure of Compound 1 is as follows:

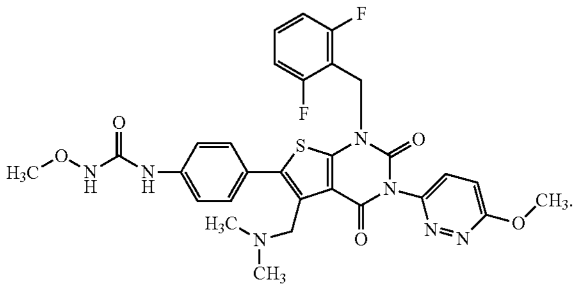 [SMILES: CONC(=O)Nc1ccc(-c2sc3c(c2CN(C)C)c(=O)n(-c2ccc(OC)nn2)c(=O)n3Cc2c(F)cccc2F)cc1]

General Information

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The Crystalline Form of the Disclosure

Form XIII is a crystalline dimethyl sulfoxide (DMSO) solvate of Compound 1. As used herein, the term "solvate" includes stoichiometric solvates and non-stoichiometric solvates, such as channel-type solvates, formed by Compound 1 and solvent. Examples of suitable solvents may include, but are not limited to, DMSO.

Form XIII of Compound 1

The present disclosure provides a crystalline form of Compound 1 characterized as Form XIII of Compound 1. In some embodiments, Form XIII of Compound 1 is a DMSO solvate. In some embodiments, Form XIII of Compound 1 is characterized by an XRPD pattern comprising at least three peaks selected from the group consisting of 5.6°, 5.9°, 9.1°, 11.4° and 14.1° 2θ±0.2° 2θ. In some embodiments, Form XIII of Compound 1 is characterized by an XRPD pattern comprising at least five peaks selected from the group consisting of 5.6°, 5.9°, 9.1°, 11.4°, 14.1°, 18.0°, 19.1°, and 21.5° 2θ±0.2° 2θ. In some embodiments, Form XIII of Compound 1 is characterized by an XRPD pattern having peaks at 5.6°, 5.9°, 9.1°, 11.4° and 14.1° 2θ±0.2° 2θ. In certain such embodiments, the XRPD pattern has one or more peaks selected from the group consisting of 18.0°, 19.1°, and 21.5°±0.2° 2θ. In some embodiments, Form XIII of Compound 1 is characterized by an XRPD pattern substantially the same as the pattern shown in FIG. 1.

Form XIII of Compound 1 may also be characterized by thermogravimetry (TG). In some embodiments, Form XIII of Compound 1 is characterized by a TG thermogram indicating continuous weight loss of about 8.6% between about 32° C. and about 120° C. In some embodiments, Form XIII of Compound 1 is characterized by a TG thermogram substantially the same as the pattern shown in FIG. 2.

Form XIII of Compound 1 may also be characterized by differential scanning calorimetry (DSC). In some embodiments, Form XIII of Compound 1 is characterized by an onset of melting between about 99° C. and about 101° C. In some embodiments, Form XIII of Compound 1 is characterized by an onset of melting at about 100° C. In some embodiments, Form XIII of Compound 1 is characterized by a differential scanning calorimetry (DSC) thermogram comprising an endothermic peak between about 105° C. and about 107° C. In some embodiments, Form XIII of Compound 1 is characterized by a DSC thermogram comprising an endothermic peak at about 106° C. In some embodiments, Form XIII of Compound 1 is characterized by a DSC thermogram substantially the same as the pattern shown in FIG. 3.

In some embodiments, Form XIII of Compound 1 is characterized by having at least two of the following:

a) an XRPD pattern comprising at least three peaks selected from the group consisting of 5.6°, 5.9°, 9.1°, 11.4° and 14.1° 2θ±0.2° 2θ;

b) an onset of melting at about 100° C. as measured by DSC; and c) an endothermic peak at about 106° C. as measured by DSC.

In some embodiments, the XRPD pattern comprises peaks at 5.6°, 5.9°, 9.1°, 11.4° and 14.1° 2θ±0.2° 2θ. In some embodiments, the XRPD pattern comprises peaks at 5.6°, 5.9°, and 9.1° 2θ±0.2° 2θ. In some embodiments, the XRPD pattern comprises peaks at 5.6°, 5.9°, and 11.4° 2θ±0.2° 2θ. In some embodiments, the XRPD pattern comprises peaks at 5.6°, 5.9°, and 14.1° 2θ±0.2° 2θ. In some embodiments, the XRPD pattern comprises peaks at 9.1°, 11.4° and 14.1°

2θ±0.2° 2θ. In some embodiments, the XRPD pattern comprises peaks at 5.9°, 11.4° and 14.1° 2θ±0.2° 2θ. In some embodiments, the XRPD pattern comprises peaks at 5.6°, 11.4° and 14.1° 2θ±0.2° 2θ. In some embodiments, the XRPD pattern comprises peaks at 5.9°, 9.1°, and 11.4° 2θ±0.2° 2θ. In some embodiments, the XRPD pattern comprises peaks at 5.6°, 9.1°, and 11.4° 2θ±0.2° 2θ. In some embodiments, the XRPD pattern comprises peaks at 5.6°, 9.1°, and 14.1° 2θ±0.2° 2θ. In some embodiments, the XRPD pattern comprises peaks at 5.9°, 9.1°, and 14.1° 2θ±0.2° 2θ. In some embodiments, the XRPD pattern comprises one or more peaks selected from the group consisting of 18.0°, 19.1°, and 21.5°±0.2° 2θ.

In some embodiments, a single crystal structure of Form XIII of Compound 1 has 1-5 molecules of DMSO and one molecule of Compound 1. In some embodiments, a single crystal structure of Form XIII of Compound 1 has one molecule of DMSO and one molecule of Compound 1. In some embodiments, a single crystal structure of Form XIII of Compound 1 has two molecules of DMSO and one molecule of Compound 1. In some embodiments, a single crystal structure of Form XIII of Compound 1 has 2.5 molecules of DMSO and one molecule of Compound 1. In some embodiments, a single crystal structure of Form XIII of Compound 1 has three molecules of DMSO and one molecule of Compound 1. In some embodiments, a single crystal structure of Form XIII of Compound 1 has four molecules of DMSO and one molecule of Compound 1. In some embodiments, a single crystal structure of Form XIII of Compound 1 has five molecules of DMSO and one molecule of Compound 1. In some embodiments, a single crystal structure of Form XIII of Compound 1 has five molecules of DMSO and two molecules of Compound 1.

In some embodiments, Form XIII of Compound 1 has about 1% to about 10% by weight DMSO relative to the total weight of Compound 1 present in Form XIII of Compound 1. In some embodiments, Form XIII of Compound 1 has about 7% to about 9% by weight DMSO relative to the total weight of Compound 1 present in Form XIII of Compound 1. In some embodiments, Form XIII of Compound 1 has about 8% to about 9% by weight DMSO relative to the total weight of Compound 1 present in Form XIII of Compound 1. In some embodiments, Form XIII of Compound 1 has about 8.6% by weight DMSO relative to the total weight of Compound 1 present in Form XIII of Compound 1.

In some embodiments, the Form XIII of Compound I disclosed herein may be characterized by XRPD patterns having peaks listed in Table 1. All peak listings are in degrees 2θ±0.2°2θ.

TABLE 1

| XRPD Peaks of Crystalline Form XIII of Compound 1 (°2θ ± 0.2° 2θ) Form XIII |
|---|
| 5.6 |
| 5.9 |
| 9.1 |
| 11.3 |
| 11.4 |
| 11.7 |
| 14.1 |
| 14.6 |
| 15.7 |
| 17.3 |
| 18.0 |
| 18.3 |

TABLE 1-continued

| XRPD Peaks of Crystalline Form XIII of Compound 1 (°2θ ± 0.2° 2θ) Form XIII |
|---|
| 19.1 |
| 20.9 |
| 21.5 |
| 21.7 |

Impurity Profile of the Crystalline Form XIII of Compound 1

Through production of Form XIII of Compound 1, the purity of the crystalline form of Compound 1 may be increased. Accordingly, Form XIII and Form I of Compound 1 with high purity may be obtained. Impurities such as U-1, U-2, and U-3 may be minimized in the desired crystalline form of Compound 1 (e.g., Forms I and XIII).

The aqueous purity of Form XIII of Compound 1 is summarized in Table 2:

TABLE 2

| HPLC Characterization of Form XIII (% area) | | | | |
|---|---|---|---|---|
| Sample | Compound 1 | U-1 | U-2 | U-3 |
| Form XIII of Compound 1 | 99.71 | 0.01 | 0.04 | 0.03 |
| THF Solvate form of Compound 1 (from U.S. Pat. No. 9,758,528) | 97.35 | 0.03 | 0.06 | 0.11 |

As shown in Table 2, Form XIII of Compound 1 is shown to have high purity and low contents of impurities U-1, U-2, and U-3. In making pharmaceutical-grade compounds, it is desirable, and in some aspects required, to minimize or control to below certain limits the amounts of impurities, as they may be inactive, toxic or have other undesired effects. In U.S. Pat. No. 9,758,528, a tetrahydrofuran (THF) solvate form of Compound 1 is disclosed as an intermediate in the production of Form I of Compound 1. The higher purity of Form XIII of Compound 1 compared to the THF solvate of Form I may enable production of higher purity Form I of Compound 1.

Preparation of Crystalline Forms of the Disclosure

Figure 4:
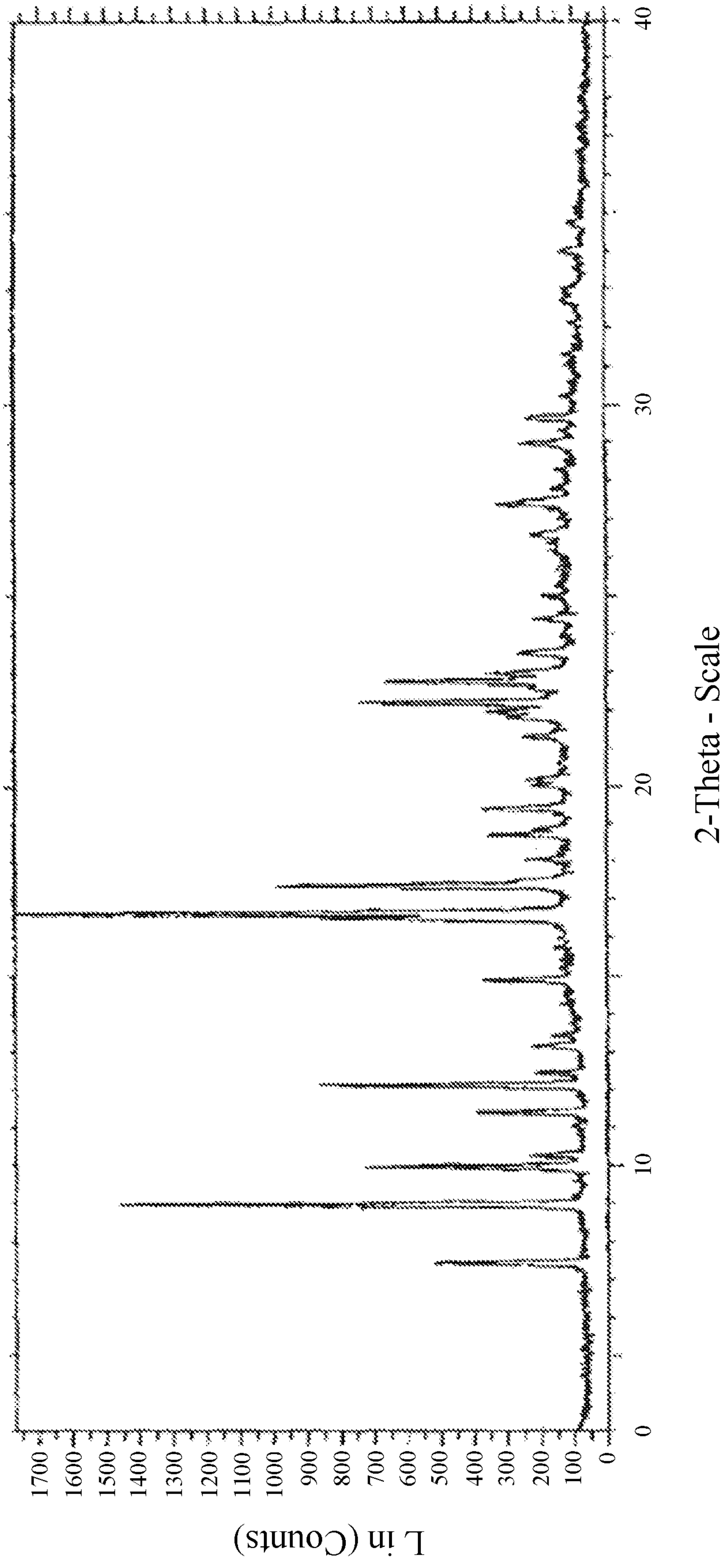
FIG. 4 depicts a powder X-ray diffraction pattern of Form I of Compound 1. Adapted from FIG. 2 of U.S. Pat. No. 9,758,528.
Figure 5:
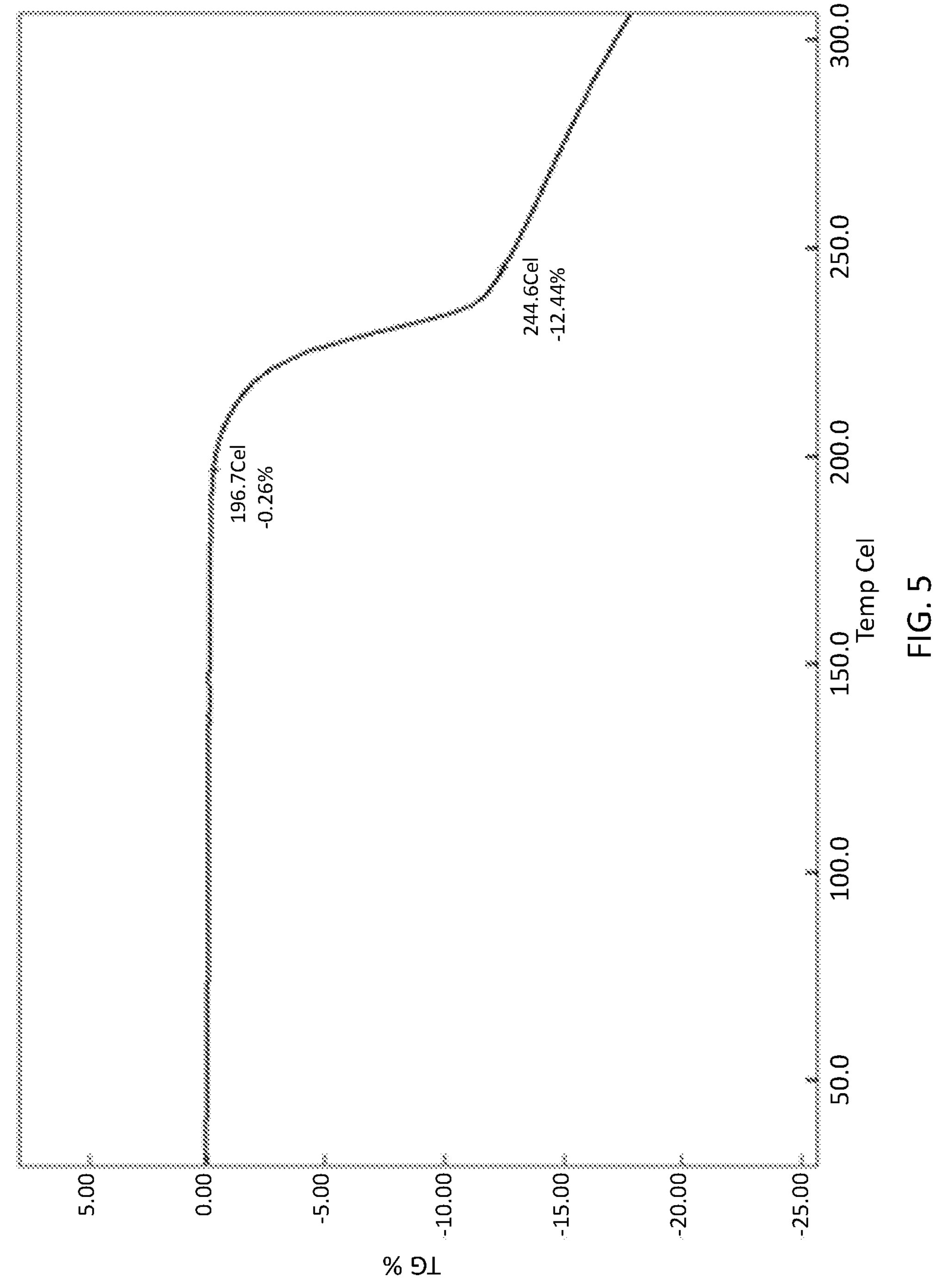
FIG. 5 depicts a TG thermogram of Form I of Compound 1.
Figure 6:
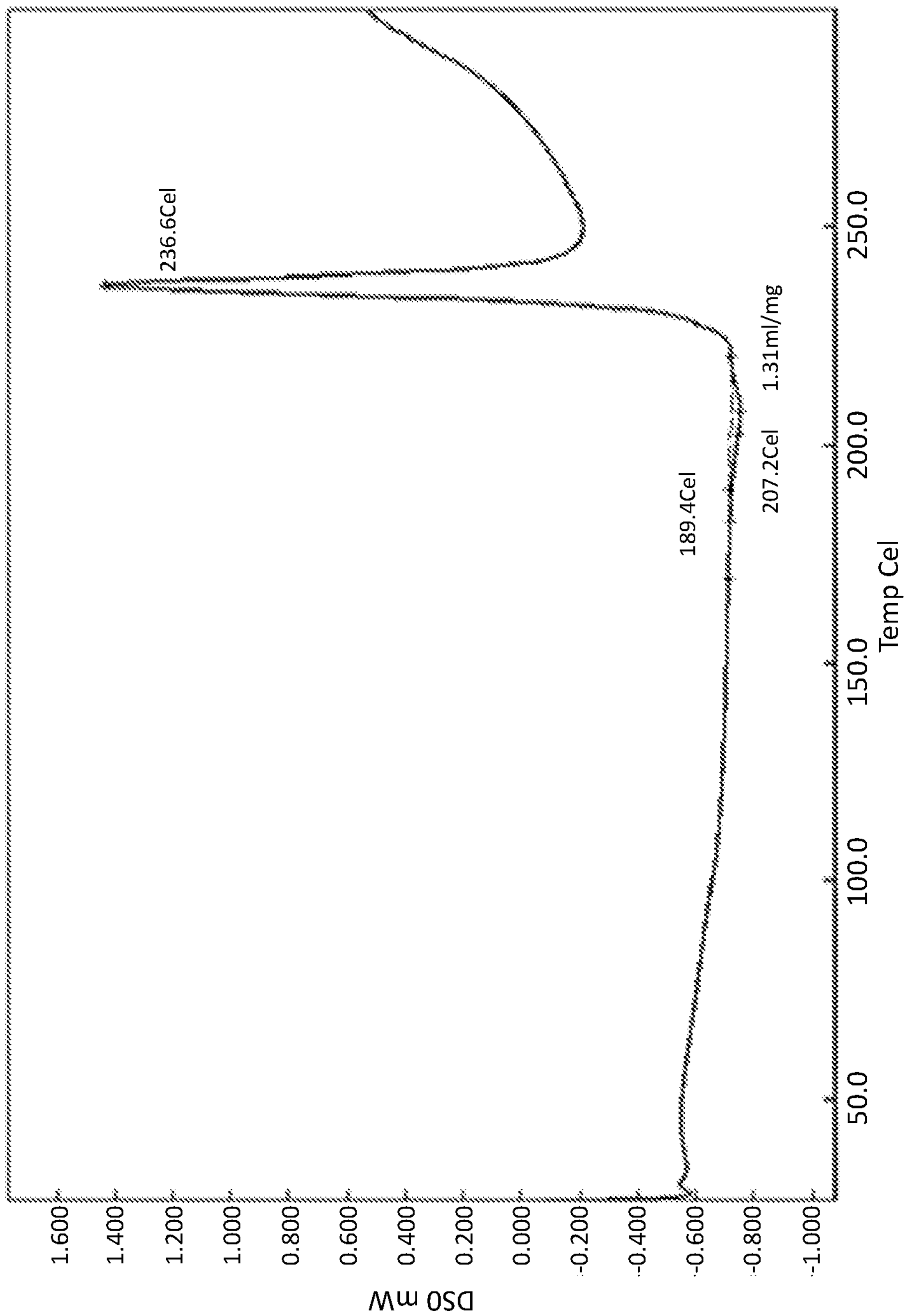
FIG. 6 depicts a DSC thermogram of Form I of Compound 1.
Figure 7:
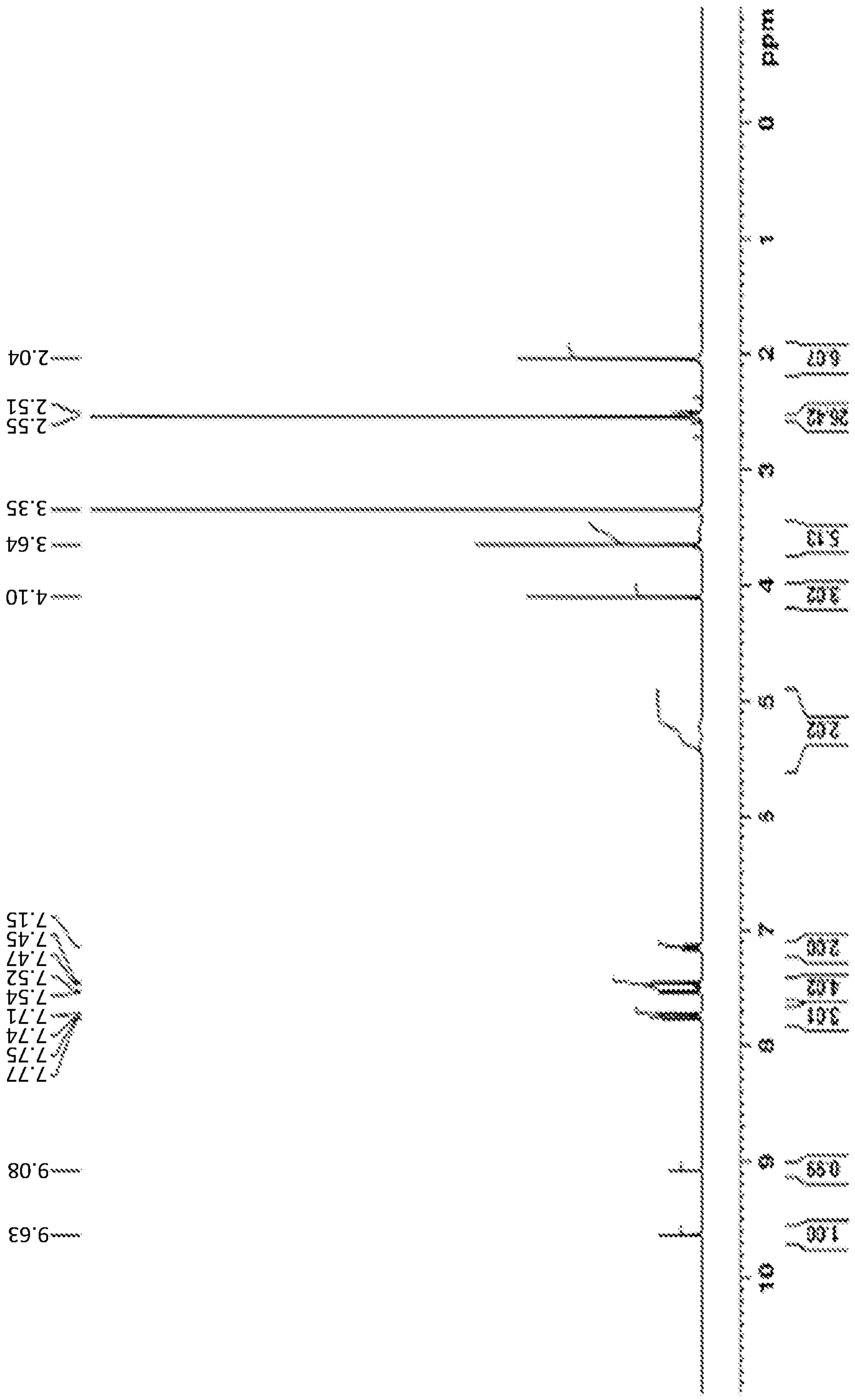
FIG. 7 depicts a $^1H$ NMR spectrum (400 MHz) of Form XIII of Compound 1. The solvent for $^1H$ NMR collection was DMSO.

Form XIII of Compound 1 may be used during the synthesis or production of Form I of Compound 1. Form I of Compound 1 and methods of preparing Form I of Compound 1 are described in U.S. Pat. No. 9,758,528, hereby incorporated by reference in its entirety, particular with regard to synthesis and crystallization methods. The XRPD pattern of Form I of Compound 1 is depicted in FIG. 4. Methods of preparing Compound 1 before crystallization are described in U.S. Pat. Nos. 7,300,935, 8,058,280, 8,735,401, and 9,346,822, hereby incorporated by reference in their entireties.

In some embodiments, Form I of Compound 1 may be made by using Form XIII of Compound 1. For example, Form I of Compound 1 may be made by suspending Form XIII of Compound 1 in DMSO:EtOH (1.7:1.2) at a temperature of about 35° C.+/−5° C. The mixture is maintained at about 35° C.+/−5° C. for about four days. Precipitated solids from a resulting suspension are recovered to afford Form I of Compound 1. In some embodiments, the mixture is seeded with a small amount of Form I of Compound 1.

In some embodiments, Form I of Compound 1 may be made by suspending Form XIII of Compound 1 in DMSO: EtOH (1.7:5.5) at a temperature of about 35° C.+/−5° C. The mixture is maintained at about 35° C.+/−5° C. for about six days. Precipitated solids from a resulting suspension are recovered to afford Form I of Compound 1. In some embodiments, the mixture is seeded with a small amount of Form I of Compound 1.

In some embodiments, Form I of Compound 1 may be made by suspending Form XIII of Compound 1 in DMSO: EtOH (1.7:5.5) at a temperature of about 25° C.+/−5° C. The mixture is maintained at about 25° C.+/−5° C. for about 11 days. Precipitated solids from a resulting suspension are recovered to afford Form I of Compound 1. In some embodiments, the mixture is seeded with a small amount of Form I of Compound 1.

In some embodiments, Form I of Compound 1 may be made by suspending Form XIII of Compound 1 in DMSO: EtOH (1.7:8.6) at a temperature of about 25° C.+/−5° C. The mixture is maintained at about 25° C.+/−5° C. for about 17 days. Precipitated solids from a resulting suspension are recovered to afford Form I of Compound 1. In some embodiments, the mixture is seeded with a small amount of Form I of Compound 1.

For example, Form I of Compound 1 may be made by suspending Form XIII of Compound 1 in DMSO:THF: EtOH (1.7:0.11:1.2) at a temperature of about 35° C.+/−5° C. The mixture is maintained at about 35° C.+/−5° C. for about four days. Precipitated solids from a resulting suspension are recovered to afford Form I of Compound 1. In some embodiments, the mixture is seeded with a small amount of Form I of Compound 1.

In some embodiments, Form I of Compound 1 may be made by suspending Form XIII of Compound 1 in DMSO: THF:EtOH (1.7:0.11:5.5) at a temperature of about 35° C.+/−5° C. The mixture is maintained at about 35° C.+/−5° C. for about six days. Precipitated solids from a resulting suspension are recovered to afford Form I of Compound 1. In some embodiments, the mixture is seeded with a small amount of Form I of Compound 1.

In some embodiments, Form I of Compound 1 may be made by suspending Form XIII of Compound 1 in DMSO: THF:EtOH (1.7:0.11:5.5) a ta temperature of about 25° C.+/−5° C. The mixture is maintained at about 25° C.+/−5° C. for about 11 days. Precipitated solids from a resulting suspension are recovered to afford Form I of Compound 1. In some embodiments, the mixture is seeded with a small amount of Form I of Compound 1.

In some embodiments, Form I of Compound 1 may be made by suspending Form XIII of Compound 1 in DMSO: THF:EtOH (1.7:0.11:8.6) at a temperature of about 25° C.+/−5° C. The mixture is maintained at about 25° C.+/−5° C. for about 17 days. Precipitated solids from a resulting suspension are recovered to afford Form I of Compound 1. In some embodiments, the mixture is seeded with a small amount of Form I of Compound 1.

The disclosure provides a method for preparing Form XIII of Compound 1. In some embodiments, a THF solvate form of Compound 1 (see U.S. Pat. No. 9,758,528) is added to a vessel containing DMSO and the solid fails to dissolve. Solid-to-solid form transitions are known in the art. Without being bound to any particular theory, the THF solvate form of Compound 1 may convert to Form XIII of Compound 1 described herein via, for example, a solid-to-solid conversion. The solids are recovered from the vessel to afford Form XIII of Compound 1.

In some embodiments, Form XIII of Compound 1 is prepared using Form I of Compound 1. In certain such embodiments, Form I of Compound 1 is suspended in DMSO at room temperature and precipitated solids from a resulting suspension are recovered to afford Form XIII of Compound 1. In some embodiments, the mixture of Form I of Compound 1 in DMSO is seeded with a small amount of Form XIII of Compound 1.

In some embodiments, the method for preparing Form XIII of Compound 1 comprises suspending Form I of Compound 1 in DMSO at room temperature; isolating a white suspension resulting from the suspension of Form I of Compound 1 in DMSO; subjecting the white suspension to a series of temperature cycles from about 15° C. to about 30° C. to about 15° C., about 10° C. to about 30° C. to about 10° C., and about 5° C. to about 35° C. to about 5° C.; and isolating precipitated solids from the white suspension to afford Form XIII of Compound 1. In some embodiments, there are six temperature cycles from about 15° C. to about 30° C. to about 15° C. In some embodiments, there are six temperature cycles from about 10° C. to about 30° C. to about 10° C. In some embodiments, there are eight temperature cycles from about 5° C. to about 35° C. to about 5° C. In some embodiments, the mixture of Form I of Compound 1 in DMSO is seeded with a small amount of Form XIII of Compound 1.

Pharmaceutical Compositions

The disclosed crystalline Form XIII of Compound 1 may be used on its own but if administered to a subject will generally be administered in the form of a pharmaceutical composition in which Form XIII of Compound 1 is in association with a pharmaceutically acceptable carrier. Conventional procedures for the selection and preparation of suitable pharmaceutical compositions are described in, for example, "Pharmaceuticals—The Science of Dosage Form Designs," M. E. Aulton, Churchill Livingstone, 1988, which is hereby incorporated by reference in its entirety.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent, such as a crystalline form of the disclosure, from one organ, or portion of the body, to another organ, or portion of the body of a subject. Carriers should be selected on the basis of compatibility and the release profile properties of the desired dosage form. Exemplary carrier materials may include, e.g., binders, suspending agents, disintegration agents, filling agents, surfactants, solubilizers, stabilizers, lubricants, wetting agents, diluents, spray-dried dispersions, and the like. See, e.g., Hoover, John E., *Remington's Pharmaceutical Sciences*, Mack Publishing Co., Easton, Pa. 1975.

In some embodiments, the disclosure provides for a pharmaceutical composition comprising one or more crystalline forms disclosed herein. In some embodiments, the disclosure provides for a pharmaceutical composition comprising only one crystalline form disclosed herein. In some embodiments, the disclosure provides for a pharmaceutical composition comprising Form XIII of Compound 1. In other embodiments, the disclosure provides for a pharmaceutical composition comprising two crystalline forms disclosed herein. For example, a pharmaceutical composition comprising Compound 1 can comprise Form I of Compound 1 and Form XIII of Compound 1.

In some embodiments, the disclosure provides for a pharmaceutical composition comprising Form XIII of Compound 1 and a pharmaceutically acceptable carrier. In some embodiments, the disclosure provides for a pharmaceutical composition comprising Form I and Form XIII of Compound 1 and a pharmaceutically acceptable carrier.

Depending on the mode of administration, the pharmaceutical composition will comprise from about 0.05 to about 99 wt % (percent by weight), more particularly from about 0.05 to about 80 wt %, still more particularly from about 0.10 to about 70 wt %, and even more particularly from about 0.10 to about 50 wt % of one or more disclosed crystalline forms, all percentages by weight being based on total composition. In some embodiments, the pharmaceutical composition is administered transdermally, transmucosally, or topically (e.g., to the skin or to mucous membranes). In some embodiments, the pharmaceutical composition is administered as a vaginal suppository.

Pharmaceutical compositions of the present disclosure may comprise a therapeutically effective amount of one or more disclosed crystalline forms formulated together with one or more pharmaceutically acceptable carriers. Examples of pharmaceutically acceptable carriers include sugars such as lactose, dextrose, mannitol, glucose and sucrose; starches such as starches derived from corn, wheat or potato and other pharmaceutical grade starches such as sodium starch glycolate; cellulose and its derivatives such as sodium carboxymethyl cellulose, methyl cellulose, ethyl cellulose, hydroxypropyl cellulose, cellulose acetate, and microcrystalline cellulose; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; lubricants such as sodium lauryl sulfate and magnesium stearate; coloring agents; releasing agents; coating agents; sweetening, flavoring and perfuming agents; preservatives and antioxidants.

Methods of Treatment and Uses

The present disclosure provides a method of treating a disorder comprising administering an effective amount of one or more crystalline forms, or one or more pharmaceutical compositions comprising said one or more crystalline forms, described herein to thereby treat the disorder in a subject in need thereof.

In some embodiments of the methods and uses of the disclosure, the disorder is a hormone-dependent condition. Hormone-dependent conditions may include sex hormone-dependent cancer (e.g., prostate cancer, uterine cancer, breast cancer, and ovarian cancer), bone metastasis of sex hormone-dependent cancer, prostatic hypertrophy, hysteromyoma (uterine fibroids), adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, heavy menstrual bleeding, and symptoms associated with these conditions. Such symptoms may include anemia, irregular periods, spotting, inflammation, pain, fatigue, urinary obstruction, urinary frequency, incontinence, constipation, anxiety, sleep disturbance, decrease in quality of life, difficulty with activities of daily living, female sexual dysfunction, and depression. In some embodiments of the methods and uses of the disclosure, the hormone-dependent condition is prostate cancer, uterine cancer, breast cancer, or ovarian cancer. Additional disorders that Compound 1 is useful for treating are described in U.S. Pat. Nos. 7,300,935, 8,058,280, 8,735,401, 9,346,822, WO2018060501, and WO2018060463, incorporated herein by reference in their entireties.

In some embodiments of the methods and uses of the disclosure, the hormone-dependent condition is prostate cancer. In some embodiments of the methods and uses of the disclosure, the hormone-dependent condition is uterine cancer. In some embodiments of the methods and uses of the disclosure, the hormone-dependent condition is breast cancer. In some embodiments of the methods and uses of the disclosure, the hormone-dependent condition is ovarian cancer. In some embodiments of the methods and uses of the disclosure, the hormone-dependent condition is uterine fibroids. In some embodiments of the methods and uses of the disclosure, the hormone-dependent condition is heavy menstrual bleeding associated with uterine fibroids. In some embodiments of the methods and uses of the disclosure, the hormone-dependent condition is pain or other symptoms associated with uterine fibroids. In some embodiments of the methods and uses of the disclosure, the hormone-dependent condition is endometriosis. In some embodiments of the methods and uses of the disclosure, the hormone-dependent condition is pain associated with endometriosis. In some embodiments of the methods and uses of the disclosure, the hormone-dependent condition is adenomyosis. In some embodiments of the methods and uses of the disclosure, the hormone-dependent condition is heavy menstrual bleeding.

A "patient" or "subject" is a mammal. Examples of mammals may include, but are not limited to, any member of the class Mammalia including humans; non-human primates such as chimpanzees, monkeys, baboons, and rhesus monkeys; cattle, horses, sheep, goats, and swine; rabbits, dogs, and cats; and rodents such as rats, mice and guinea pigs. In some embodiments, the patient or subject is a human.

The terms "effective amount" or "therapeutically effective amount" when used in connection with one or more crystalline forms or pharmaceutical compositions of the disclosure may refer to a sufficient amount of the one or more crystalline forms or pharmaceutical compositions to provide the desired biological result. That result can be reduction and/or alleviation of the signs, symptoms, or causes of a disorder, or any other desired alteration of a biological system. For example, an "effective amount" for therapeutic use may be the amount of the one or more pharmaceutical compositions comprising the one or more crystalline forms as disclosed herein required to provide a clinically significant decrease in a disorder. An appropriate "effective amount" in any individual case may be determined by one of ordinary skill in the art using routine experimentation.

As used herein, the terms "treat" or "treatment" or cognates thereof, are meant to indicate a postponement of development of disorders; and/or reducing severity of such symptoms that will or are expected to develop. Thus, these terms may include ameliorating existing disorder symptoms; preventing additional symptoms; ameliorating or preventing the underlying causes of symptoms; inhibiting the disorder, e.g., arresting the development of the disorder; relieving the disorder; causing regression of the disorder; relieving a symptom caused by the disorder; or stopping or alleviating the symptoms of the disorder.

The terms "administered," "administration," or "administering" as used in this disclosure may refer to either directly administering one or more crystalline forms or pharmaceutical compositions of the disclosure to a subject.

The present disclosure provides a method of treating a disorder comprising administering an effective amount of Form XIII of Compound 1 to thereby treat the disorder in a subject in need thereof. The present disclosure provides a method of treating a disorder comprising administering an effective amount of a mixture of Forms I and XIII of Compound 1 to thereby treat the disorder in a subject in need thereof. In some embodiments, the disorder is a hormone-dependent condition.

The present disclosure provides a method of treating a disorder comprising administering an effective amount of one or more pharmaceutical compositions of the present disclosure to thereby treat the disorder in a subject in need thereof. In some embodiments, the present disclosure provides a method of treating a disorder comprising administering an effective amount of one or more pharmaceutical compositions comprising one or more crystalline forms disclosed herein to thereby treat the disorder in a subject in need thereof. In some embodiments, the present disclosure provides a method of treating a disorder comprising administering an effective amount of one or more pharmaceutical compositions comprising Form XIII of Compound 1 to thereby treat the disorder in a subject in need thereof. In some embodiments, the present disclosure provides a method of treating a disorder comprising administering an effective amount of one or more pharmaceutical compositions comprising a mixture of Forms I and XIII of Compound 1 to thereby treat the disorder in a subject in need thereof. In some embodiments, the disorder is a hormone-dependent condition.

The present disclosure provides one or more crystalline forms of the present disclosure or one or more pharmaceutical compositions of the present disclosure for use in treating a disorder in a subject in need thereof. In some embodiments, the one or more crystalline forms comprise Form XIII of Compound 1. In some embodiments, the one or more crystalline forms are a mixture of Forms I and XII of Compound 1. In some embodiments, the one or more pharmaceutical compositions of the present disclosure comprise one or more crystalline forms disclosed herein. In some embodiments, the one or more pharmaceutical compositions of the present disclosure comprise Form XIII of Compound 1. In some embodiments, the one or more pharmaceutical compositions of the present disclosure comprise a mixture of Forms I and XIII of Compound 1. In some embodiments, the disorder is a hormone-dependent condition.

The present disclosure provides for use of one or more crystalline forms of the present disclosure for treating a disorder in a subject in need thereof. In some embodiments, the present disclosure provides for use of Form XIII of Compound 1 for treating a disorder in a subject in need thereof. In some embodiments, the present disclosure provides for use of a mixture of Forms I and XIII of Compound 1 for treating a disorder in a subject in need thereof. In some embodiments, the disorder is a hormone-dependent condition.

The present disclosure provides for use of one or more pharmaceutical compositions of the present disclosure for treating a disorder in a subject in need thereof. In some embodiments, the present disclosure provides for use of one or more pharmaceutical compositions comprising one or more crystalline forms disclosed herein for treating a disorder in a subject in need thereof. In some embodiments, the present disclosure provides for use of one or more pharmaceutical compositions comprising Form XIII of Compound 1 for treating a disorder in a subject in need thereof. In some embodiments, the present disclosure provides for use of one or more pharmaceutical compositions comprising a mixture of Forms I and XIII of Compound 1 for treating a disorder in a subject in need thereof. In some embodiments, the disorder is a hormone-dependent condition.

The present disclosure provides for use of one or more crystalline forms of the present disclosure in the manufacture of a medicament for treating a disorder. In some embodiments, the present disclosure provides for use of Form XIII of Compound 1 in the manufacture of a medicament for treating a disorder. In some embodiments, the present disclosure provides for use of a mixture of Forms I and XII of Compound 1 in the manufacture of a medicament for treating a disorder. In some embodiments, the disorder is a hormone-dependent condition.

The present disclosure provides for use of one or more pharmaceutical compositions of the present disclosure in the manufacture of a medicament for treating a disorder. In some embodiments, the present disclosure provides for use of one or more pharmaceutical compositions comprising one or more crystalline forms disclosed herein in the manufacture of a medicament for treating a disorder. In some embodiments, the present disclosure provides for use of one or more pharmaceutical compositions comprising Form XIII of Compound 1 in the manufacture of a medicament for treating a disorder. In some embodiments, the present disclosure provides for use of one or more pharmaceutical compositions comprising a mixture of Forms I and XIII of Compound 1 in the manufacture of a medicament for treating a disorder. In some embodiments, the disorder is a hormone-dependent condition.

The present disclosure provides for use of one or more crystalline forms of the present disclosure as a medicament for treating a disorder. In some embodiments, the present disclosure provides for use of Form XIII of Compound 1 as a medicament for treating a disorder. In some embodiments, the present disclosure provides for use of a mixture of Forms I and XIII of Compound 1 as a medicament for treating a disorder. In some embodiments, the disorder is a hormone-dependent condition.

The present disclosure provides for use of one or more pharmaceutical compositions of the present disclosure as a medicament for treating a disorder. In some embodiments, the present disclosure provides for use of one or more pharmaceutical compositions comprising one or more crystalline forms disclosed herein as a medicament for treating a disorder. In some embodiments, the present disclosure provides for use of one or more pharmaceutical compositions comprising Form XIII of Compound 1 as a medicament for treating a disorder. In some embodiments, the present disclosure provides for use of one or more pharmaceutical compositions comprising a mixture of Forms I and XIII of Compound 1 as a medicament for treating a disorder. In some embodiments, the disorder is a hormone-dependent condition.

In some embodiments of the methods and uses of the disclosure, only one pharmaceutical composition of the disclosure is used in the methods or uses. In some embodiments of the methods and uses of the disclosure, only one crystalline form of the disclosure is used in the methods or uses.

For the therapeutic uses mentioned herein, the dosage administered will, of course, vary with the one or more crystalline forms or pharmaceutical compositions employed, the mode of administration, the treatment desired and the disorder indicated. For example, the daily dosage of the one or more crystalline forms of the present disclosure, if inhaled, may be in the range from about 0.05 micrograms per kilogram body weight (μg/kg) to about 100 micrograms per kilogram body weight (μg/kg). Alternatively, if the one or more crystalline forms or pharmaceutical compositions is administered orally, then the daily dosage of the one or more crystalline forms of the present disclosure may be in the range from about 0.01 micrograms per kilogram body weight (μg/kg) to about 100 milligrams per kilogram body weight (mg/kg).

It will be understood, however, that the total daily usage of the one or more crystalline forms or pharmaceutical compositions of the present disclosure will be decided by the attending physician within the scope of sound medical judgment. The specific therapeutically effective dose level for any particular patient will depend upon a variety of factors including the disorder being treated and the severity of the disorder; the activity of the specific crystalline form employed; the specific pharmaceutical composition employed; the age, body weight, general health, sex and diet of the patient; the time of administration, route of administration, and rate of excretion of the specific crystalline form employed; the duration of the treatment; drugs used in combination or coincidental with the specific crystalline form employed; and like factors well known in the medical arts. A physician or veterinarian of ordinary skill in the art can readily determine and prescribe the therapeutically effective amount of the one or more crystalline forms or pharmaceutical compositions disclosed herein required to treat, counter, or arrest the progress of the disorder.

Combination Therapy

In some embodiments, one or more crystalline forms or pharmaceutical compositions described herein may be used alone or together or conjointly administered, or used in combination, with one or more other therapeutic agents or pharmaceutical compositions. Conjoint administration or used in combination may refer to any form of administration of two or more different compounds, crystalline forms, or pharmaceutical compositions such that the second compound, crystalline form, or pharmaceutical composition is administered while the previously administered compound, crystalline form, or pharmaceutical composition is still effective in the body. For example, the different compounds, crystalline forms, or pharmaceutical compositions can be administered either in the same formulation or in a separate formulation, either simultaneously, sequentially, or by separate dosing of the individual components of the treatment. In some embodiments, the different compounds, crystalline forms, or pharmaceutical compositions can be administered within about one hour, about 12 hours, about 24 hours, about 36 hours, about 48 hours, about 72 hours, or about a week of one another. Thus, an individual who receives such treatment can benefit from a combined effect of different compounds, crystalline forms, or pharmaceutical compositions.

In some embodiments, one or more of the crystalline forms or pharmaceutical compositions of the disclosure are used in combination with one or more other crystalline forms or pharmaceutical compositions of the disclosure in the methods or uses of the disclosure. In certain such embodiments, the combination of one or more other crystalline forms or pharmaceutical compositions of the disclosure is used in a method for treating one or more of the disorders listed herein.

In some embodiments, one or more of the crystalline forms or pharmaceutical compositions of the disclosure are used in combination with estradiol or a corresponding amount of estradiol equivalent. In some embodiments, one or more of the crystalline forms or pharmaceutical compositions of the disclosure are used in combination with a progestin. In some embodiments, one or more of the crystalline forms or pharmaceutical compositions of the disclosure are used in combination with estradiol or a corresponding amount of estradiol equivalent and a progestin. In some embodiments, the progestin is norethindrone acetate.

In some embodiments, combinations of one or more crystalline forms or pharmaceutical compositions provided herein, or combinations of other known agents or pharmaceutical compositions and one or more crystalline forms or pharmaceutical compositions provided herein, are formulated into pharmaceutical compositions and medicaments that are useful in the methods and uses of the disclosure. The disclosure also provides for use of such combinations in treating one or more of the disorders listed herein.

In some embodiments of the disclosure, one or more crystalline forms or pharmaceutical compositions of the disclosure are administered at a sub-therapeutic dose, wherein a subtherapeutic dose is a dose that would be insufficient to treat one of the disorders listed herein if administered alone.

Kits

In some embodiments, this disclosure also provides a pharmaceutical package or kit comprising one or more containers filled with at least one crystalline form or pharmaceutical composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

The foregoing applies to any of the crystalline forms, pharmaceutical compositions, methods, and uses described herein. This disclosure specifically contemplates any combination of the features of such crystalline forms, pharmaceutical compositions, methods, and uses (alone or in combination) with the features described for the various kits described in this section.

Although methods and materials similar or equivalent to those described herein can be used in the practice or testing of the present disclosure, illustrative methods and materials are described herein. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

ENUMERATED EMBODIMENTS

Some embodiments of the disclosure include those of Embodiment I:

Embodiment I-1. A crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form XIII of Compound 1.

Embodiment I-2. The crystalline form of Embodiment I-1, characterized by an X-ray power diffraction pattern comprising at least three peaks selected from the group consisting of 5.6°, 5.9°, 9.1°, 11.4° and 14.1° 2θ±0.2° 2θ.

Embodiment I-3. The crystalline form of Embodiment I-1, characterized by an X-ray power diffraction pattern comprising at least five peaks selected from the group consisting of 5.6°, 5.9°, 9.1°, 11.4°, 14.1°, 18.0°, 19.1°, and 21.5° 2θ±0.2° 2θ.

Embodiment I-4. The crystalline form of Embodiment I-1, characterized by an X-ray power diffraction pattern comprising peaks at 5.6°, 5.9°, 9.1°, 11.4° and 14.1° 2θ±0.2° 2θ.

Embodiment I-5. The crystalline form of Embodiment I-4, wherein the X-ray power diffraction pattern comprises one or more peaks selected from the group consisting of 18.0°, 19.1°, and 21.5°±0.2° 2θ.

Embodiment I-6. The crystalline form of any one of Embodiments I-1 to I-5, characterized by an XRPD pattern substantially the same as the pattern shown in FIG. 1.

Embodiment I-7. The crystalline form of any one of Embodiments I-1 to I-6, characterized by a thermogravimetric (TG) thermogram indicating continuous weight loss of about 8.6% between about 32° C. and about 120° C.

Embodiment I-8. The crystalline form of any one of Embodiments I-1 to I-7, characterized by a TG thermogram substantially the same as the pattern shown in FIG. 2.

Embodiment I-9. The crystalline form of any one of Embodiments I-1 to I-8, characterized by an onset of melting between about 99° C. and about 101° C.

Embodiment I-10. The crystalline form of any one of Embodiments I-1 to I-9, characterized by an onset of melting at about 100° C.

Embodiment I-11. The crystalline form of any one of Embodiments I-1 to I-10, characterized by a differential scanning calorimetry (DSC) thermogram comprising an endothermic peak between about 105° C. and about 107° C.

Embodiment I-12. The crystalline form of any one of Embodiments I-1 to I-11, characterized by a DSC thermogram comprising an endothermic peak at about 106° C.

Embodiment I-13. The crystalline form of any one of Embodiments I-1 to I-12, characterized by a DSC thermogram substantially the same as the pattern shown in FIG. 3.

Embodiment I-14. The crystalline form of Embodiment I-1, characterized by having at least two of the following:

a) an XRPD pattern comprising at least three peaks selected from the group consisting of 5.6°, 5.9°, 9.1°, 11.4° and 14.1° 2θ±0.2°2θ;

b) an onset of melting at about 100° C. as measured by DSC; and c) an endothermic peak at about 106° C. as measured by DSC.

Embodiment I-15. A pharmaceutical composition comprising one or more crystalline forms of any one of Embodiments I-1 to I-14 and a pharmaceutically acceptable carrier.

Embodiment I-16. The pharmaceutical composition of Embodiment I-15, the pharmaceutical composition comprising a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl) phenyl)-N'-methoxyurea characterized as Form I of Compound 1.

Embodiment I-17. A method of treating a disorder in a subject in need thereof, comprising administering to the subject an effective amount of one or more crystalline forms of any one of Embodiments I-1 to I-14.

Embodiment I-18. The method of Embodiment I-17, the method comprising administering to the subject an effective amount of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1.

Embodiment I-19. A method of treating a disorder in a subject in need thereof, comprising administering to the subject an effective amount of the pharmaceutical composition of Embodiment I-15 or I-16.

Embodiment I-20. The method of any one of Embodiments I-17 to I-19, wherein the disorder is a hormone-dependent condition.

Embodiment I-21. The method of Embodiment I-20, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-22. The method of Embodiment I-20 or I-21, wherein the hormone-dependent condition is prostate cancer, uterine cancer, breast cancer, or ovarian cancer.

Embodiment I-23. The method of any one of Embodiments I-20 to I-22, wherein the hormone-dependent condition is prostate cancer.

Embodiment I-24. The method of any one of Embodiments I-20 to I-22, wherein the hormone-dependent condition is uterine cancer.

Embodiment I-25. The method of any one of Embodiments I-20 to I-22, wherein the hormone-dependent condition is breast cancer.

Embodiment I-26. The method of any one of Embodiments I-20 to I-22, wherein the hormone-dependent condition is ovarian cancer.

Embodiment I-27. The method of Embodiment I-20 or I-21, wherein the hormone-dependent condition is uterine fibroids.

Embodiment I-28. The method of Embodiment I-20, wherein the hormone-dependent condition is heavy menstrual bleeding associated with uterine fibroids.

Embodiment I-29. The method of Embodiment I-20, wherein the hormone-dependent condition is pain or other symptoms associated with uterine fibroids.

Embodiment I-30. The method of Embodiment I-20 or I-21, wherein the hormone-dependent condition is endometriosis.

Embodiment I-31. The method of Embodiment I-20 or I-21, wherein the hormone-dependent condition is adenomyosis.

Embodiment I-32. The method of Embodiment I-20 or I-21, wherein the hormone-dependent condition is heavy menstrual bleeding.

Embodiment I-33. The method of any one of Embodiments I-17 to I-33, the method comprising administering to the subject estradiol or a corresponding amount of estradiol equivalent.

Embodiment I-34. The method of any one of Embodiments I-17 to I-33, the method comprising administering to the subject a progestin.

Embodiment I-35. The method of any one of Embodiments I-17 to I-33, the method comprising administering to the subject estradiol, or a corresponding amount of estradiol equivalent, and a progestin.

Embodiment I-36. The method of Embodiment I-34 or I-35, wherein the progestin is norethindrone acetate.

Embodiment I-37. One or more crystalline forms of any one of Embodiments I-1 to I-14 for use in treating a disorder in a subject in need thereof.

Embodiment I-38. The one or more crystalline forms for use of Embodiment I-37, the one or more crystalline forms for use comprising a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 for use in treating the disorder in the subject in need thereof.

Embodiment I-39. The one or more crystalline forms for use of Embodiment I-37 or I-96, wherein the disorder is a hormone-dependent condition.

Embodiment I-40. The one or more crystalline forms for use of Embodiment I-39, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-41. The one or more crystalline forms for use of Embodiment I-39 or I-40, wherein the hormone-dependent condition is prostate cancer, uterine cancer, breast cancer, or ovarian cancer.

Embodiment I-42. The one or more crystalline forms for use of any one of Embodiments 1-39 to I-41, wherein the hormone-dependent condition is prostate cancer.

Embodiment I-43. The one or more crystalline forms for use of any one of Embodiments 1-39 to I-41, wherein the hormone-dependent condition is uterine cancer.

Embodiment I-44. The one or more crystalline forms for use of any one of Embodiments 1-39 to I-41, wherein the hormone-dependent condition is breast cancer.

Embodiment I-45. The one or more crystalline forms for use of any one of Embodiments 1-39 to I-41, wherein the hormone-dependent condition is ovarian cancer.

Embodiment I-46. The one or more crystalline forms for use of Embodiment I-39 or I-40, wherein the hormone-dependent condition is uterine fibroids.

Embodiment I-47. The one or more crystalline forms for use of Embodiment I-39, wherein the hormone-dependent condition is heavy menstrual bleeding associated with uterine fibroids.

Embodiment I-48. The one or more crystalline forms for use of Embodiment I-39, wherein the hormone-dependent condition is pain or other symptoms associated with uterine fibroids.

Embodiment I-49. The one or more crystalline forms for use of Embodiment I-39 or I-40, wherein the hormone-dependent condition is endometriosis.

Embodiment I-50. The one or more crystalline forms for use of Embodiment I-39 or I-40, wherein the hormone-dependent condition is adenomyosis.

Embodiment I-51. The one or more crystalline forms for use of Embodiment I-39 or I-40, wherein the hormone-dependent condition is heavy menstrual bleeding.

Embodiment I-52. The one or more crystalline forms for use of any one of Embodiments 1-37 to I-51, wherein the one or more crystalline forms for use are used in combination with estradiol or a corresponding amount of estradiol equivalent.

Embodiment I-53. The one or more crystalline forms for use of any one of Embodiments 1-37 to I-51, wherein the one or more crystalline forms for use are used in combination with progestin.

Embodiment I-54. The one or more crystalline forms for use of any one of Embodiments 1-37 to I-51, wherein the one or more crystalline forms for use are used in combination with estradiol, or a corresponding amount of estradiol equivalent, and a progestin.

Embodiment I-55. The one or more crystalline forms for use of Embodiment I-53 or I-54, wherein the progestin is norethindrone acetate.

Embodiment I-56. A pharmaceutical composition of Embodiment I-15 or I-16 for use in treating a disorder in a subject in need thereof.

Embodiment I-57. The pharmaceutical composition for use of Embodiment I-56, wherein the disorder is a hormone-dependent condition.

Embodiment I-58. The pharmaceutical composition for use of Embodiment I-57, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-59. The pharmaceutical composition for use of Embodiment I-57 or I-58, wherein the hormone-dependent condition is prostate cancer, uterine cancer, breast cancer, or ovarian cancer.

Embodiment I-60. The pharmaceutical composition for use of any one of Embodiments 1-57 to I-59, wherein the hormone-dependent condition is prostate cancer.

Embodiment I-61. The pharmaceutical composition for use of any one of Embodiments 1-57 to I-59, wherein the hormone-dependent condition is uterine cancer.

Embodiment I-62. The pharmaceutical composition for use of any one of Embodiments 1-57 to I-59, wherein the hormone-dependent condition is breast cancer.

Embodiment I-63. The pharmaceutical composition for use of any one of Embodiments 1-57 to I-59, wherein the hormone-dependent condition is ovarian cancer.

Embodiment I-64. The pharmaceutical composition for use of Embodiment I-57 or I-58, wherein the hormone-dependent condition is uterine fibroids.

Embodiment I-65. The pharmaceutical composition for use of Embodiment I-57, wherein the hormone-dependent condition is heavy menstrual bleeding associated with uterine fibroids.

Embodiment I-66. The pharmaceutical composition for use of Embodiment I-57, wherein the hormone-dependent condition is pain or other symptoms associated with uterine fibroids.

Embodiment I-67. The pharmaceutical composition for use of Embodiment I-57 or I-58, wherein the hormone-dependent condition is endometriosis.

Embodiment I-68. The pharmaceutical composition for use of Embodiment I-57 or I-58, wherein the hormone-dependent condition is adenomyosis.

Embodiment I-69. The pharmaceutical composition for use of Embodiment I-57 or I-58, wherein the hormone-dependent condition is heavy menstrual bleeding.

Embodiment I-70. The pharmaceutical composition for use of any one of Embodiments 1-56 to I-69, wherein the pharmaceutical composition for use is used in combination with estradiol or a corresponding amount of estradiol equivalent.

Embodiment I-71. The pharmaceutical composition for use of any one of Embodiments 1-56 to I-69, wherein the pharmaceutical composition for use is used in combination with a progestin.

Embodiment I-72. The pharmaceutical composition for use of any one of Embodiments 1-56 to I-69, wherein the pharmaceutical composition for use is used in combination with estradiol, or a corresponding amount of estradiol equivalent, and a progestin.

Embodiment I-73. The pharmaceutical composition for use of Embodiment I-71 or I-72, wherein the progestin is norethindrone acetate.

Embodiment I-74. Use of one or more crystalline forms of any one of Embodiments I-1 to I-14 for treating a disorder in a subject in need thereof.

Embodiment I-75. The use of Embodiment I-74, the use comprising use of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 for treating the disorder in the subject in need thereof.

Embodiment I-76. Use of a pharmaceutical composition of Embodiment I-15 or I-16 for treating a disorder in a subject in need thereof.

Embodiment I-77. Use of one or more crystalline forms of any one of Embodiments I-1 to I-14 in the manufacture of a medicament for treating a disorder.

Embodiment I-78. The use of Embodiment I-77, the use comprising use of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in the manufacture of the medicament for treating the disorder.

Embodiment I-79. Use of a pharmaceutical composition of Embodiment I-15 or I-16 in the manufacture of a medicament for treating a disorder.

Embodiment I-80. Use of one or more crystalline forms of any one of Embodiments I-1 to I-14 as a medicament for treating a disorder.

Embodiment I-81. The use of Embodiment I-80, the use comprising use of a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 as a medicament for treating the disorder.

Embodiment I-82. Use of a pharmaceutical composition of Embodiment I-15 or I-16 as a medicament for treating a disorder.

Embodiment I-83. The use of any one of Embodiments I-74 to I-82, wherein the disorder is a hormone-dependent condition.

Embodiment I-84. The use of Embodiment I-83, wherein the hormone-dependent condition is sex hormone-dependent cancer, prostate cancer, uterine cancer, breast cancer, ovarian cancer, bone metastasis of sex hormone-dependent cancer, prostatic hypertrophy, hysteromyoma, adenomyoma, metrofibroma, precocious puberty, amenorrhea, premenstrual syndrome, dysmenorrhea, multilocular ovary syndrome, polycystic ovary syndrome, acne, infertility, hot flash, endometriosis, adenomyosis, or heavy menstrual bleeding.

Embodiment I-85. The use of Embodiment I-83 or I-84, wherein the hormone-dependent condition is prostate cancer, uterine cancer, breast cancer, or ovarian cancer.

Embodiment I-86. The use of any one of Embodiments I-83 to I-85, wherein the hormone-dependent condition is prostate cancer.

Embodiment I-87. The use of any one of Embodiments I-83 to I-85, wherein the hormone-dependent condition is uterine cancer.

Embodiment I-88. The use of any one of Embodiments I-83 to I-85, wherein the hormone-dependent condition is breast cancer.

Embodiment I-89. The use of any one of Embodiments I-83 to I-85, wherein the hormone-dependent condition is ovarian cancer.

Embodiment I-90. The use of Embodiment I-83 or I-84, wherein the hormone-dependent condition is uterine fibroids.

Embodiment I-91. The use of Embodiment I-83, wherein the hormone-dependent condition is heavy menstrual bleeding associated with uterine fibroids.

Embodiment I-92. The use of Embodiment I-83, wherein the hormone-dependent condition is pain or other symptoms associated with uterine fibroids.

Embodiment I-93. The use of Embodiment I-83 or I-84, wherein the hormone-dependent condition is endometriosis.

Embodiment I-94. The use of Embodiment I-83 or I-84, wherein the hormone-dependent condition is adenomyosis.

Embodiment I-95. The use of Embodiment I-83 or I-84, wherein the hormone-dependent condition is heavy menstrual bleeding.

Embodiment I-96. The use of any one of Embodiments I-74 to I-95, the use comprising use of estradiol or a corresponding amount of estradiol equivalent for treating the disorder.

Embodiment I-97. The use of any one of Embodiments I-74 to I-95, the use comprising use of a progestin for treating the disorder.

Embodiment I-98. The use of any one of Embodiments I-74 to I-95, the use comprising use of estradiol, or a corresponding amount of estradiol equivalent, and a progestin for treating the disorder.

Embodiment I-99. The use of Embodiment I-97 or I-98, wherein the progestin is norethindrone acetate.

Embodiment I-100. A method for preparing the crystalline form of any one of Embodiments I-1 to I-14, said method comprising:

a) suspending a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in DMSO at room temperature;

b) isolating a white suspension resulting from step a); and c) isolating precipitated solids from the white suspension to afford Form XIII of Compound 1.

Embodiment I-101. A method for preparing the crystalline form of any one of Embodiments I-1 to I-14, said method comprising:

a) suspending a crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea characterized as Form I of Compound 1 in DMSO at room temperature;

b) isolating a white suspension resulting from step a);

c) subjecting the white suspension to a series of temperature cycles from about 15° C. to about 30° C. to about 15° C., about 10° C. to about 30° C. to about 10° C., and about 5° C. to about 35° C. to about 5° C.; and d) isolating precipitated solids from the white suspension to afford Form XIII of Compound 1.

EXAMPLES

General Methods of the Examples

X-Ray Powder Diffraction (XRPD)

X-ray powder diffractograms were with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the Si 111 peak position. A specimen of the sample was sandwiched between 3 μm thick films and analyzed in transmission geometry. A beam-stop, short anti-scatter extension, and an anti-scatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The location of the peaks along the x-axis (° 2θ) in both the figures and the tables were determined using proprietary software (TRIADS™ v2.1). Peak position variabilities are given to within ±0.2° 2θ based upon recommendations outlined in the USP discussion of variability in X-ray powder diffraction (United States Pharmacopeia, USP 42-NF 37 through S1, <941>, *Characterization of Crystalline and Partially Crystalline Solids by X-Ray Powder Diffraction* (*XRPD*), official from Aug. 1, 2019). For d-space listings, the wavelength used to calculate d-spacings was 1.5405929 Å, the Cu-Kα1 wavelength (*Phys. Rev.* A56(6) 4554-4568 (1997)).

Differential Scanning calorimeter (DSC)

Differential scanning calorimetry was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, and the weight was accurately recorded. The pan lid was pierced then inserted into the DSC cell. A weighed aluminum pan configured as the sample pan was placed on the reference side of the cell. Data was collected from −30° C. to 350° C. at 10° C./min.

Thermogravimetry (TG)

The TG analyses were performed using a TA Instrument Q5000 thermogravimetric analyzer. Temperature calibration was performed using nickel and Alumel™. The sample was placed in a platinum pan and inserted into the TG furnace. The furnace was heated under a nitrogen purge to 350° C. at a rate of 10° C./min.

Preparation and Characterization of Form XIII Compound 1

Form I of Compound 1

The disclosure provides methods for preparing Form I of Compound 1.

Method 1: Form I of Compound 1 may be made by using Form XIII of Compound 1. For example, Form I of Compound 1 may be made by suspending Form XIII of Compound 1 in DMSO:EtOH (1.7:1.2) at a temperature of about 35° C.+/−5° C. The mixture is maintained at about 35° C.+/−5° C. for about four days. Precipitated solids from a resulting suspension are recovered to afford Form I of Compound 1. In some experiments, the mixture is seeded with a small amount of Form I of Compound 1.

Method 2: Form I of Compound 1 may be made by suspending Form XIII of Compound 1 in DMSO:EtOH (1.7:5.5) at a temperature of about 35° C.+/−5° C. The mixture is maintained at about 35° C.+/−5° C. for about six days. Precipitated solids from a resulting suspension are recovered to afford Form I of Compound 1. In some experiments, the mixture is seeded with a small amount of Form I of Compound 1.

Method 3: Form I of Compound 1 may be made by suspending Form XIII of Compound 1 in DMSO:EtOH (1.7:5.5) at a temperature of about 25° C.+/−5° C. The mixture is maintained at about 25° C.+/−5° C. for about 11 days. Precipitated solids from a resulting suspension are recovered to afford Form I of Compound 1. In some experiments, the mixture is seeded with a small amount of Form I of Compound 1.

Method 4: Form I of Compound 1 may be made by suspending Form XIII of Compound 1 in DMSO:EtOH (1.7:8.6) at a temperature of about 25° C.+/−5° C. The mixture is maintained at about 25° C.+/−5° C. for about 17 days. Precipitated solids from a resulting suspension are recovered to afford Form I of Compound 1. In some experiments, the mixture is seeded with a small amount of Form I of Compound 1.

Method 5: Form I of Compound 1 may be made by suspending Form XIII of Compound 1 in DMSO:THF:EtOH (1.7:0.11:1.2) at a temperature of about 35° C.+/−5° C. The mixture is maintained at about 35° C.+/−5° C. for about four days. Precipitated solids from a resulting suspension are recovered to afford Form I of Compound 1. In some experiments, the mixture is seeded with a small amount of Form I of Compound 1.

Method 6: Form I of Compound 1 may be made by suspending Form XIII of Compound 1 in DMSO:THF:EtOH (1.7:0.11:5.5) at a temperature of about 35° C.+/−5° C. The mixture is maintained at about 35° C.+/−5° C. for about six days. Precipitated solids from a resulting suspension are recovered to afford Form I of Compound 1. In some experiments, the mixture is seeded with a small amount of Form I of Compound 1.

Method 7: Form I of Compound 1 may be made by suspending Form XIII of Compound 1 in DMSO:THF:EtOH (1.7:0.11:5.5) at a temperature of about 25° C.+/−5° C. The mixture is maintained at about 25° C.+/−5° C. for about 11 days. Precipitated solids from a resulting suspension are recovered to afford Form I of Compound 1. In some experiments, the mixture is seeded with a small amount of Form I of Compound 1.

Method 8: Form I of Compound 1 may be made by suspending Form XIII of Compound 1 in DMSO:THF:EtOH (1.7:0.11:8.6) at a temperature of about 25° C.+/−5° C. The mixture is maintained at about 25° C.+/−5° C. for about 17 days. Precipitated solids from a resulting suspension are recovered to afford Form I of Compound 1. In some experiments, the mixture is seeded with a small amount of Form I of Compound 1.

Form XIII of Compound 1

The disclosure provides methods for preparing Form XIII of Compound 1.

Method 1: A vessel was charged with DMSO (1.4 V). A THF solvate form of Compound 1 (see U.S. Pat. No. 9,758,528) was then added (1.0 equiv.) The solids failed to dissolve in the solution. The solids were recovered to afford Form XIII of Compound 1.

Method 2: A clear solution of Compound 1, Form I was prepared in DMSO at ambient temperature when spontaneous precipitation occurred. A portion of the resulting white thick suspension was subjected to series of temperature cycling experiments that included 6 cycles of 15° C. to about 30° C. to about 15° C., 6 cycles of about 10° C. to about 30° C. to about 10° C., and 8 cycles of 5° C. to about 35° C. to about 5° C. A few of the produced acicular particles possessed single crystal quality and size. A Crystal16™ was used to perform the temperature cycling experiments. In some experiments, the suspension is seeded with a small amount of Form XIII of Compound 1.

Method 3: Form I of Compound 1 is suspended in DMSO at room temperature and after 6-17 days, precipitated solids from the resulting suspension are recovered to afford Form XIII of Compound 1. In some experiments, the suspension is seeded with a small amount of Form XIII of Compound 1.

XRPD Characterization of Form XIII of Compound 1

XRPD data for the crystalline Form XIII of Compound 1 disclosed herein was collected as detailed above. The XRPD pattern for Form XIII of Compound 1 is detailed in FIG. 1. The peaks present in this XRPD pattern are listed in Table 1 above. All peak listings are in degrees 2θ±0.2° 2θ. A single crystal structure of Form XIII of Compound 1 was found to have one molecule of Compound 1 and 2.5 molecules of DMSO associated (or two molecules of Compound 1 and 5 molecules of DMSO).

Thermal Analyses (DSC and TG) of Form XIII of Compound 1

DSC and TG data for Form XIII of Compound 1 disclosed herein were collected as detailed above. The TG thermogram for Form XIII of Compound 1 is detailed in FIG. 2. The DSC thermogram for Form XIII of Compound 1 is detailed in FIG. 3. The thermal events in the DSC and TG of Form XIII of Compound 1 are detailed in the table below.

| Thermal events in DSC and TG of Form XIII | |
|---|---|
| DSC | Overlapping broad endotherm at 74.5° C.<br>With large endotherm at 106.0° C.<br>(onset 100.2° C.) |
| TG | 3.3% wt loss at 32-85° C.<br>5.3% wt loss at 85-120° C.<br>(0.75 mole DMSO are ~8.6 wt %) |

Impurity Characterization Present in Form XIII of Compound 1

The amounts of the impurities U-1, U-2, and U-3 present in Form XIII of Compound 1 were determined by HPLC. The aqueous purity of Form XIII of Compound 1 is summarized in the table below:

HPLC Characterization of Form XIII (% area)

| Sample | Compound 1 | U-1 | U-2 | U-3 |
|---|---|---|---|---|
| Form XIII of Compound 1 | 99.71 | 0.01 | 0.04 | 0.03 |
| THF Solvate form of Compound 1 (from U.S. Pat. No. 9,758,528) | 97.35 | 0.03 | 0.06 | 0.11 |

HPLC data was collected using a Waters-system containing an Alliance™ HPLC system with Empower software. The column used was Inertsil ODS-4, 4.6 mm×150 mm, 3 μm (GL Sciences Corp.). The HPLC method was as follows:

| HPLC Method | |
|---|---|
| 50 mM Phosphate Solution | Dissolve 11.5 g of ammonium dihydrogenphosphate in 2000 mL of water. |
| Solvent | Mix 1600 mL of 50 mM phosphate solution with 400 mL acetonitrile (volume ratio 4:1). |
| 50 mM Phosphate Buffer pH 2.4 | Dissolve 28.75 g of ammonium dihydrogenphosphate in 5000 mL of water. Add phosphoric acid to obtain pH 2.4. |
| Mobile phase A | Mix 4200 mL of 50 mM phosphate buffer pH 2.4 (corresponding to 4200 g) with 400 mL acetonitrile (corresponding to 314 g) and 400 mL THF (corresponding to 356 g) (volume ratio 21:2:2). |
| Mobile phase B | Mix 800 mL of 50 mM phosphate buffer pH 2.4 (corresponding to 800 g) with 1200 mL acetonitrile (corresponding to 943 g) (volume ratio 2:3) |
| Needle wash | Mix 800 mL water with 200 mL acetonitrile |
| Flow | 1.0 mL/min |
| Temperature | Column: 40° C.<br>Sample: 5° C. |
| Detection | Spectrophotometric at: 290 nm |
| Detector settings for PDA | Resolution: 4.8 nm<br>Sampling rate: 2 points/sec<br>Filter Time Constant: 1.0 sec. (normal) |
| Detector settings for TUV | Sampling rate: 2 points/sec<br>Filter Time Constant: 1.0 sec. (normal) |
| Registration time | 70 min |

| Gradient table | Time (min.) | Mobile phase A (%) | Mobile phase B (%) |
|---|---|---|---|
| | Start | 100 | 0 |
| | 35.0 | 100 | 0 |

-continued

| | | |
|---|---|---|
| 60.0 | 0 | 100 |
| 60.1 | 100 | 0 |
| 70.0 | 100 | 0 |

| Compound | Retention Time (min) |
|---|---|
| U-1 | 13.62 |
| U-2 | 16.10 |
| Compound 1 | 24.97 |
| U-3* | 42.16 |

*Due to chromatographic effects, the retention time of U-3 may vary.

We claim:

1. A crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea that exhibits an X-ray powder diffraction pattern comprising at least three 2-theta (2θ±0.2° 2θ) peaks selected from 5.6°, 5.9°, 9.1°, 11.4°, and 14.1°.

2. The crystalline form of claim 1, characterized by an X-ray powder diffraction pattern comprising at least five 2-theta (2θ±0.2° 2θ) peaks selected from 5.6°, 5.9°, 9.1°, 11.4°, 14.1°, 18.0°, 19.1°, and 21.5°.

3. The crystalline form of claim 1, characterized by an X-ray powder diffraction pattern comprising 2-theta (2θ+0.2° 2θ) peaks at 5.6°, 5.9°, 9.1°, 11.4° and 14.1°.

4. The crystalline form of claim 3, wherein the X-ray powder diffraction pattern further comprises one or more 2-theta (2θ+0.2° 2θ) peaks selected from 18.0°, 19.1°, and 21.5°.

5. The crystalline form of claim 1, characterized by an X-ray powder diffraction pattern as shown in FIG. 1.

6. The crystalline form of claim 1, characterized by a thermogravimetric (TG) thermogram indicating continuous weight loss of 8.6% between 32° C. and 120° C.

Figure 2:
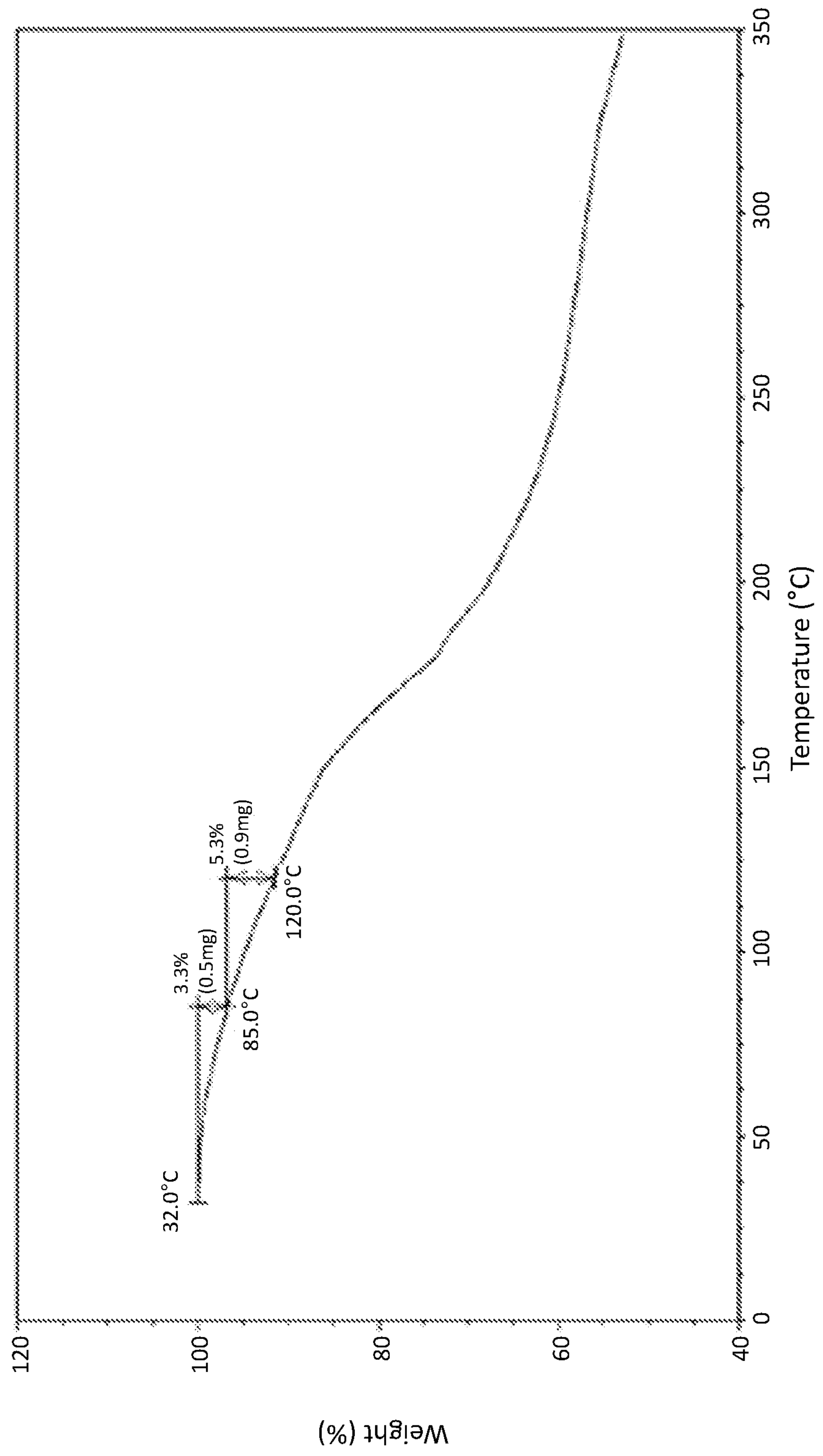
FIG. 2 depicts a thermogravimetry (TG) thermogram of Form XIII of Compound 1.

7. The crystalline form of claim 1, characterized by a TG thermogram as shown in FIG. 2.

8. The crystalline form of claim 1, characterized by an onset of melting between 99° C. and 101° C.

9. The crystalline form of claim 1, characterized by an onset of melting at 100° C.

10. The crystalline form of claim 1, characterized by a differential scanning calorimetry (DSC) thermogram comprising an endothermic peak between 105° C. and 107° C.

11. The crystalline form of claim 1, characterized by a DSC thermogram comprising an endothermic peak at 106° C.

Figure 3:
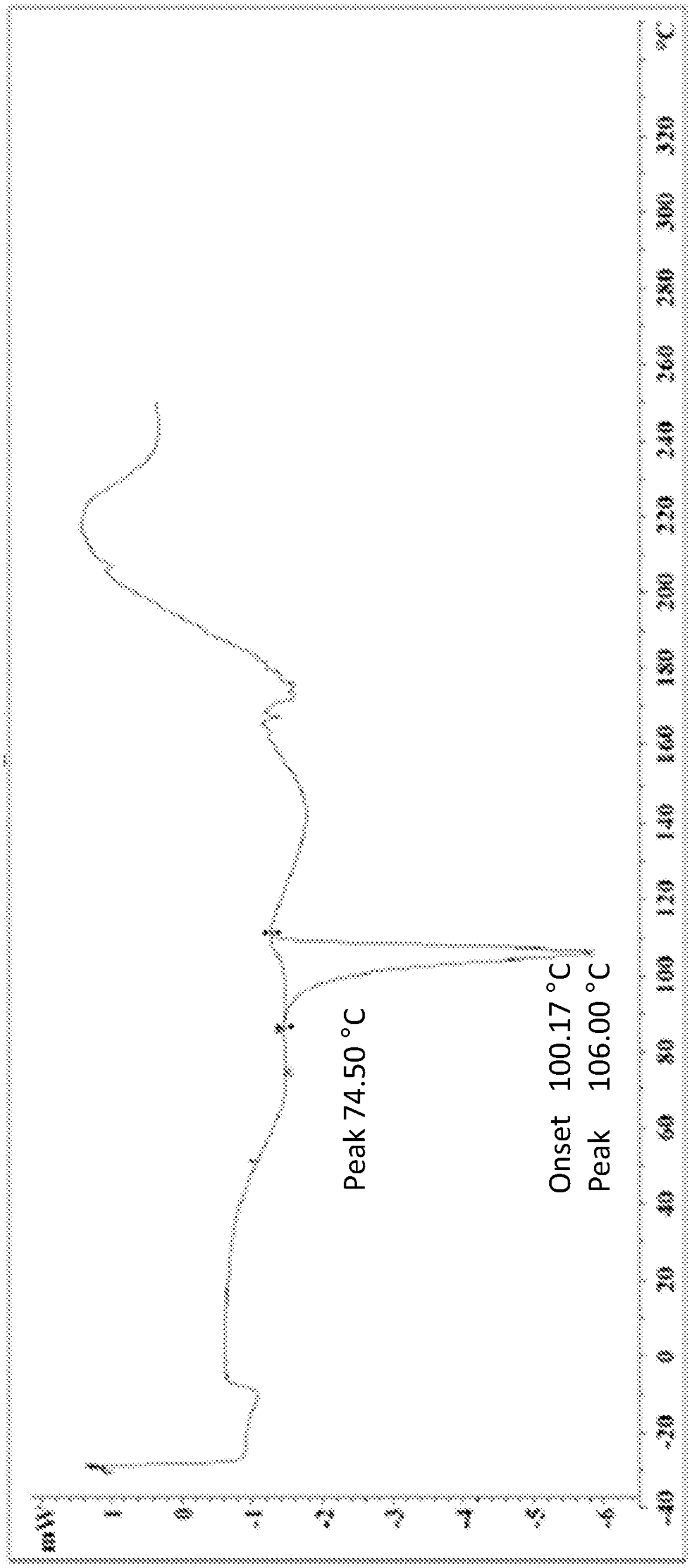
FIG. 3 depicts a differential scanning calorimetry (DSC) thermogram of Form XIII of Compound 1.

12. The crystalline form of claim 1, characterized by a DSC thermogram as shown in FIG. 3.

13. The crystalline form of claim 1, characterized by having at least one of the following:

a) an onset of melting at 100° C. as measured by DSC; and b) an endothermic peak at 106° C. as measured by DSC.

14. A pharmaceutical composition comprising the crystalline form of claim 1 and a pharmaceutically acceptable carrier.

15. A method for preparing a crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, said method comprising:

a) suspending an anhydrous crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in DMSO at room temperature;

b) isolating a white suspension resulting from step a); and c) isolating precipitated solids from the white suspension to afford the crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, wherein the crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is characterized by an X-ray powder diffraction pattern comprising at least three 2-theta (2θ+0.2° 2θ) peaks selected from 5.6°, 5.9°, 9.1°, 11.4°, and 14.1°.

16. A method for preparing a crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, said method comprising:

a) suspending an anhydrous crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in DMSO at room temperature;

b) isolating a white suspension resulting from step a);

c) subjecting the white suspension to a series of temperature cycles from 15° C. to 30° C. to 15° C., 10° C. to 30° C. to 10° C., and 5° C. to 35° C. to 5° C.; and d) isolating precipitated solids from the white suspension to afford the crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea wherein the crystalline form of a dimethyl sulfoxide solvate of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea is characterized by an X-ray powder diffraction pattern comprising at least three 2-theta (2θ+0.2° 2θ) peaks selected from 5.6°, 5.9°, 9.1°, 11.4°, and 14.1°.

17. The crystalline form of claim 1, wherein a single crystal structure of the crystalline form comprises one to five molecules of DMSO and one molecule of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea.

18. The method of claim 15, wherein the anhydrous crystalline form of N-(4-(1-(2,6-difluorobenzyl)-5-((dimethylamino)methyl)-3-(6-methoxy-3-pyridazinyl)-2,4-dioxo-1, 2,3,4-tetrahydrothieno[2,3-d]pyrimidin-6-yl)phenyl)-N'-methoxyurea in step a) is characterized by an X-ray powder diffraction pattern comprising 2-theta (2θ) peaks at approximately 7.4°, 8.9°, 9.9°, 12.1°, 16.6°, 17.3°, 22.2°, 22.8°, and 27.4°.

19. The method of claim 16, wherein the anhydrous crystalline form of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea in step a) is characterized by an X-ray powder diffraction pattern comprising 2-theta (2θ) peaks at approximately 7.4°, 8.9°, 9.9°, 12.1°, 16.6°, 17.3°, 22.2°, 22.8°, and 27.4°.

* * * * *